(12) United States Patent
Ernst et al.

(10) Patent No.: US 11,512,040 B2
(45) Date of Patent: Nov. 29, 2022

(54) PROCESS FOR PREPARATION OF AMINO ALCOHOLS

(71) Applicants: BASF SE, Ludwigshafen am Rhein (DE); BASF CORPORATION, Florham Park, NJ (US); THE REGENTS OF THE UNIVERSITY OF CALIFORNIA, Oakland, CA (US)

(72) Inventors: Martin Ernst, Heidelberg (DE); Stephan Zuend, Fremont, CA (US); Bo Su, Berkeley, CA (US); Ala Bunescu, Cambridge (GB); John F. Hartwig, Berkeley, CA (US)

(73) Assignees: BASF SE, Ludwigshafen am Rhein (DE); BASF CORPORATION, Florham Park, NJ (US); THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 119 days.

(21) Appl. No.: 17/257,080

(22) PCT Filed: Jul. 2, 2019

(86) PCT No.: PCT/US2019/040254
§ 371 (c)(1),
(2) Date: Dec. 30, 2020

(87) PCT Pub. No.: WO2020/010055
PCT Pub. Date: Jan. 9, 2020

(65) Prior Publication Data
US 2021/0155575 A1 May 27, 2021

Related U.S. Application Data

(60) Provisional application No. 62/693,240, filed on Jul. 2, 2018.

(51) Int. Cl.
*C07C 213/00* (2006.01)

(52) U.S. Cl.
CPC .................................. *C07C 213/00* (2013.01)

(58) Field of Classification Search
None
See application file for complete search history.

(56) References Cited

PUBLICATIONS

International Search Report and Written Opinion in International Application No. PCT/US2019/040254, dated Oct. 17, 2019.

Liu et al., "Site-selective C-H arylation of primary aliphatic amines enabled by a catalytic transient directing group," Nature Chemistry, vol. 9, pp. 26-32 (2017).
McNally et al., "Palladium-catalysed C-H activation of aliphatic amines to give strained nitrogen heterocycles," Nature, vol. 510, pp. 129-138 (2014).
Smalley et al., "Mechanistic Insights into the Palladium-Catalyzed Aziridination of Aliphatic Amines by C-H Activation," J. Am. Chem. Soc. 137, 10632-10641 (2015).
Studer et al., "Catalytic Hydrogenation of Chiral alpha-Amino and alpha-Hydroxy Esters at Room Temperature with Nishimura Catalyst without Racemization," Advanced Synthesis & Catalysis, vol. 343, No. 8, pp. 802-808 (2001).
Wang et al., "Versatile Synthesis of Free and N-Benzyloxycarbonyl-Protected 2,2-Disubstituted Taurines," European Journal of Organic Chemistry, vol. 2008, No. 2, pp. 350-355 (2008).
Wille et al., "1-substituted 1,4-dihydro-3,5-pyridinedicarbaldehydes," Monatshefte fur Chemie / Chemical Monthly, vol. 110, No. 3, pp. 613-638(1979).
Wu et al., "Pd-Catalyzed gamma-C(sp3)-H Arylation of Free Amines Using a Transient Directing Group," J. Am. Chem. Soc. 138, 14554-14557 (2016).
Yada et al., "Buttressing Salicylaldehydes: A Multipurpose Directing Group for C(sp3)-H Bond Activation," Angew. Chem. Int. Ed. 56, 1073-1076 (2017).

*Primary Examiner* — Sudhakar Katakam
*Assistant Examiner* — Jennifer C Sawyer
(74) *Attorney, Agent, or Firm* — Grüneberg and Myers PLLC

(57) ABSTRACT

A process for the preparation of amino alcohols includes condensing a compound of Formula (II), a stereoisomer, a tautomer, or a salt thereof with a compound of Formula (IIIa) or Formula (IIIb), a stereoisomer, a tautomer, or a salt thereof to form a condensation product; hydroxylating or acyloxylating the condensation product in the presence of an oxidant to obtain a hydroxylation or acyloxylation product; and subjecting the hydroxylation or acyloxylation product to one or more subsequent reactions comprising a hydrolysis reaction, alcohol deprotection, an amino lysis reaction, or a combination of two or more thereof to obtain an amino alcohol of Formula (I).

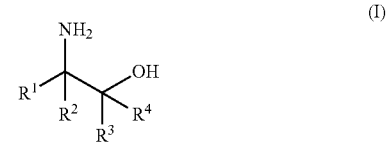

20 Claims, No Drawings

PROCESS FOR PREPARATION OF AMINO ALCOHOLS

CROSS-REFERENCE TO RELATED APPLICATIONS

This application is a U.S. National Phase Application under 35 U.S.C. § 371 of International Application No. PCT/US2019/040254, filed on Jul. 2, 2019, which claims the benefit of and priority to U.S. Patent Application No. 62/693,240, filed on Jul. 2, 2018, the entire disclosures of which are incorporated herein in their entirety.

FIELD

The present technology is generally related to a process for preparing amino alcohols. In particular, the present technology relates to a process for preparing 1,2-amino alcohols from the hydroxylation or acyloxylation of primary alkyl amines.

SUMMARY

In an aspect of the present technology, a process for preparing an amino alcohol is provided, the process comprising: condensing a compound of Formula (II), a stereoisomer, a tautomer, or a salt thereof with a compound of Formula (IIIa) or Formula (IIIb), a stereoisomer, a tautomer, or a salt thereof to form a condensation product; hydroxylating or acyloxylating the condensation product in the presence of an oxidant to obtain a hydroxylation or acyloxylation product; and subjecting the hydroxylation or acyloxylation product to one or more subsequent reactions comprising a hydrolysis reaction, alcohol deprotection, an aminolysis reaction, or a combination of two or more thereof to obtain an amino alcohol of Formula (I); wherein:

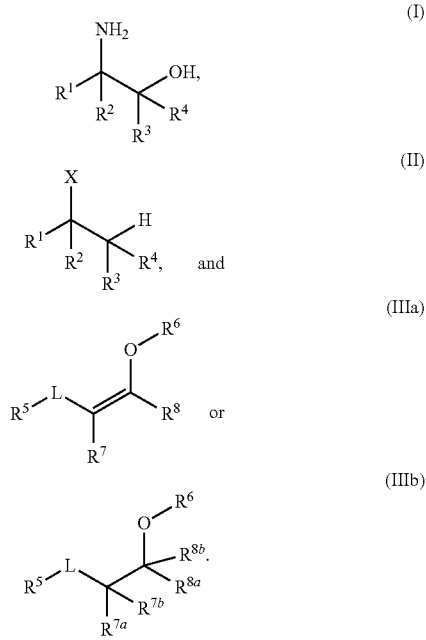

In the above structures, L is a carbonyl, imine, acetal, or hemiacetal; X is an amine or a protected amine; $R^1$, $R^2$, $R^3$, and $R^4$ are each independently a hydrogen, a substituted or unsubstituted $C_1$-$C_{10}$ alkyl, a substituted or unsubstituted $C_3$-$C_{10}$ cycloalkyl, a substituted or unsubstituted aryl, a substituted or unsubstituted heterocyclyl, a substituted or unsubstituted heteroaryl, or two or more of $R^1$, $R^2$, $R^3$, and $R^4$ together with the atoms to which they are attached form a substituted or unsubstituted cycloalkyl, substituted or unsubstituted heterocyclyl, substituted or unsubstituted aromatic, or substituted or unsubstituted heteroaromatic ring; $R^5$ is a hydrogen, halogen, a hydroxyl, an alkoxy, an O-acyl, a substituted or unsubstituted $C_1$-$C_{10}$ alkyl, a substituted or unsubstituted $C_3$-$C_{10}$ cycloalkyl, a substituted or unsubstituted aryl, a substituted or unsubstituted heterocyclyl, or a substituted or unsubstituted heteroaryl; $R^6$ is a hydrogen, a substituted or unsubstituted $C_1$-$C_{10}$ alkyl, a substituted or unsubstituted $C_3$-$C_{10}$ cycloalkyl, a substituted or unsubstituted aryl, a substituted or unsubstituted heterocyclyl, or a substituted or unsubstituted heteroaryl; $R^7$ and $R^8$ in Formula (IIIa) are each independently a hydrogen, a substituted or unsubstituted $C_1$-$C_{10}$ alkyl, a substituted or unsubstituted $C_3$-$C_{10}$ cycloalkyl, a substituted or unsubstituted aryl, a substituted or unsubstituted heterocyclyl, a substituted or unsubstituted heteroaryl, or $R^7$ and $R^8$ together with the atoms to which they are attached form a substituted or unsubstituted aromatic or heteroaromatic ring; and $R^{7a}$, $R^{7b}$, $R^{8a}$, and $R^{8b}$ in Formula (IIIb) are each independently a hydrogen, a substituted or unsubstituted $C_1$-$C_{10}$ alkyl, a substituted or unsubstituted $C_3$-$C_{10}$ cycloalkyl, a substituted or unsubstituted aryl, a substituted or unsubstituted heterocyclyl, a substituted or unsubstituted heteroaryl, or two or more of $R^{7a}$, $R^{7b}$, $R^{8a}$, and $R^{8b}$ together with the atoms to which they are attached form a substituted or unsubstituted cycloalkyl or heterocyclyl ring.

DETAILED DESCRIPTION

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

In general, "substituted" refers to an alkyl, alkenyl, alkynyl, aryl, or ether group, as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group will be substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, alkynoxy, aryloxy, and heterocyclyloxy, groups; carbonyls (oxo); carboxyls; esters; urethanes; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like. In some embodiments, as noted herein, the substitution may be with an alkyl or other carbon containing group when attached to an alkyl, cycloalkyl, aryl, heteroaryl, or heterocyclyl group.

As used herein, the term "alkyl" refers to a branched or unbranched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In certain embodiments, an alkyl comprises one to six carbon atoms (e.g., $C_1$-$C_6$ alkyl). In certain embodiments, an alkyl comprises one to three carbon atoms (e.g., $C_1$-$C_3$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). The alkyl is attached to the rest of the molecule by a single bond, for example, methyl (Me), ethyl (Et), n-propyl, 1-methylethyl (iso-propyl), n-butyl, n-pentyl, 1,1-dimethylethyl (t-butyl), 3-methylhexyl, 2-methylhexyl, and the like. In some embodiments, an alkyl group is optionally substituted by one or more of the following substituents: halo, cyano, nitro, oxo, thioxo, —$OR^a$, —$SR^a$, —$OC(O)$—$R^b$, —$N(R^a)_2$, —$C(O)R^a$, —$C(O)OR^a$, —$C(O)N(R^a)_2$, —$N(R^a)C(O)OR^a$, —$N(R^a)C(O)R^a$, $N(R^a)S(O)_2R^b$, —$S(O)_2OR^a$ and —$S(O)_2N(R^a)_2$, where each $R^a$ is independently hydrogen, alkyl, fluoroalkyl, cycloalkyl, aryl, heterocyclyl, or heteroaryl and each $R^b$ is independently alkyl, fluoroalkyl, cycloalkyl, cycloalkylalkyl, aryl, aralkyl, heterocyclyl, or heteroaryl. Examples of branched alkyl groups include, but are not limited to, isopropyl, iso-butyl, sec-butyl, tert-butyl, neopentyl, isopentyl, and 2,2 dimethylpropyl groups.

The term "aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from six to eighteen carbon atoms, where at least one of the rings in the ring system is fully unsaturated, i.e., it contains a cyclic, delocalized (4n+2) π-electron system in accordance with the Hückel theory. In some embodiments, aryl group has 6- to 10-carbon atoms. Aryl groups include, but are not limited to, groups such as phenyl, fluorenyl, and naphthyl. In some embodiments, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted cycloalkyl, optionally substituted heterocyclyl, optionally substituted heteroaryl, —$R^c$—$OR^a$, —$R^c$—$OC(O)$—$R^b$, —$R^c$—$N(R^a)_2$, —$R^c$—$C(O)R^a$, —$R^c$—$C(O)OR^a$, —$R^c$—$C(O)N(R^a)_2$, —$R^c$—$O$—$R^d$—$C(O)N(R^a)_2$, —$R^c$—$N(R^a)C(O)OR^a$, —$R^c$—$N(R^a)C(O)R^a$, —$R^c$—$N(R^a)S(O)_2R^b$, —$R^c$—$S(O)_2OR^a$ and —$R^c$—$S(O)_2N(R^a)_2$, where each $R^a$ is independently hydrogen, alkyl, fluoroalkyl, cycloalkyl, aryl (optionally substituted with one or more halo groups), heterocyclyl, or heteroaryl, each $R^b$ is independently alkyl, fluoroalkyl, cycloalkyl, aryl, heterocyclyl, or heteroaryl, each $R^c$ is independently a direct bond or a straight or branched alkylene, alkenylene, or alkynylene chain, and $R^d$ is a straight or branched alkylene, alkenylene, or alkynylene chain, and where each of the above substituents is unsubstituted unless otherwise indicated.

The term "cycloalkyl" refers to a stable non-aromatic monocyclic or polycyclic hydrocarbon radical consisting solely of carbon and hydrogen atoms, which may include fused or bridged ring systems, having from three to fifteen carbon atoms. Examples of monocyclic cycloalkyls include, e.g., cyclopropyl, cyclobutyl, cyclopentyl, cyclohexyl, cycloheptyl, and cyclooctyl. Examples of monocyclic cycloalkenyls include, e.g., cyclopentenyl, cyclohexenyl, cycloheptenyl, and cyclooctenyl. Polycyclic cycloalkyl radicals include, for example, adamantyl, norbornyl (i.e., bicyclo[2.2.1]heptanyl), norbornenyl, decalinyl,7,7-dimethyl-bicyclo[2.2.1]heptanyl, and the like. In some embodiments, the term "cycloalkyl" is meant to include cycloalkyl radicals that are optionally substituted by one or more substituents independently selected from alkyl, alkenyl, alkynyl, halo, fluoroalkyl, oxo, thioxo, cyano, nitro optionally substituted aryl, optionally substituted cycloalkyl, optionally substituted heterocyclyl, or optionally substituted heteroaryl, —$R^c$—$OR^a$, —$R^c$—$SR^a$, —$R^c$—$OC(O)$—$R^b$, —$R^c$—$N(R^a)_2$, —$R^c$—$C(O)R^a$, —$R^c$—$C(O)OR^a$, —$R^c$—$C(O)N(R^a)_2$, —$R^c$—$O$—$R^d$—$C(O)N(R^a)_2$, —$R^c$—$N(R^a)C(O)OR^a$, —$R^c$—$N(R^a)C(O)R^a$, —$R^c$—$N(R^a)S(O)_2R^b$, —$R^c$—$S(O)_2OR^a$ and —$R^c$—$S(O)_2N(R^a)_2$ where each $R^a$ is independently hydrogen, alkyl, fluoroalkyl, cycloalkyl, aryl (optionally substituted with one or more halo groups), heterocyclyl, or heteroaryl, each $R^b$ is independently alkyl, fluoroalkyl, cycloalkyl, aryl, heterocyclyl, or heteroaryl, and each $R^c$ is independently a direct bond or a straight or branched alkylene, alkenylene, or alkynylene chain.

The term "heterocyclyl" refers to a stable 4- to 18-membered nonaromatic ring radical that comprises three to twelve carbon atoms and from one to six heteroatoms selected from nitrogen, oxygen and sulfur. Unless stated otherwise specifically in the specification, the heterocyclyl radical is a monocyclic, bicyclic, tricyclic or tetracyclic ring system, which may include fused or bridged ring systems. The heteroatoms in the heterocyclyl radical may be optionally oxidized. In some embodiments, one or more nitrogen atoms, if present, are optionally quaternized. The heterocyclyl radical is partially or fully saturated. The heterocyclyl may be attached to the rest of the molecule through any atom of the ring(s). Examples of such heterocyclyl radicals include, but are not limited to, dioxolanyl, thienyl[1,3] dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. In some embodiments, the term "heterocyclyl" is meant to include heterocyclyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, $-R^c-OR^a$, $-R^c-SR^a$, $-R^c-OC(O)-R^b$, $-R^c-N(R^a)_2$, $-R^c-C(O)R^a$, $-R^c-C(O)OR^a$, $-R^c-C(O)N(R^a)_2$, $-R^c-O-R^d-C(O)N(R^a)_2$, $-R^c-N(R^a)C(O)OR^a$, $-R^c-N(R^a)C(O)R^a$, $-R^c-N(R^a)S(O)_2R^b$, $-R^c-S(O)_2OR^a$ and $-R^c-S(O)_2N(R^a)_2$, where each $R^a$ is independently hydrogen, alkyl, fluoroalkyl, cycloalkyl, cycloalkylalkyl, aryl (optionally substituted with one or more halo groups), heterocyclyl, or heteroaryl, each $R^b$ is independently alkyl, fluoroalkyl, cycloalkyl, aryl, heterocyclyl, or heteroaryl, and each $R^c$ is independently a direct bond or a straight or branched alkylene, alkenylene, or alkynylene chain.

The term "heteroaryl" refers to a radical derived from a 5- to 18-membered aromatic ring radical that comprises one to seventeen carbon atoms and from one to six heteroatoms selected from nitrogen, oxygen, and sulfur. As used herein, the heteroaryl radical may be a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. In some embodiments, the heteroatom(s) in the heteroaryl radical is optionally oxidized. In some embodiments, one or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7 dihydro-5Hcyclopenta[4,5]thieno[2,3-d]pyrimidinyl, 5,6-dihydrobenzo[h]quinazolinyl, 5,6 dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10 hexahydrocycloocta[d]pyrimidinyl, 5,6,7,8,9,10-hexahydrocycloocta[d]pyridazinyl, 5,6,7,8,9,10 hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8 tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1-H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8 tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pyridinyl, and thiophenyl (i.e., thienyl). In some embodiments, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, $-R^cOR^a$, $-R^c-SR^a$, $-R^c-OC(O)-R^b$, $-R^c-N(R^a)_2$, $-R^c-C(O)R^a$, $-R^c-C(O)OR^a$, $-R^c-C(O)N(R^a)_2$, $-R^c-O-R^d-C(O)N(R^a)_2$, $-R^c-N(R^a)C(O)OR^a$, $-R^c-N(R^a)C(O)R^a$, $-R^c-N(R^a)S(O)_2R^b$, $-R^c-S(O)_2OR^a$ and $-R^c-S(O)_2N(R^a)_2$, where each $R^a$ is independently hydrogen, alkyl, fluoroalkyl, cycloalkyl, aryl (optionally substituted with one or more halo groups), heterocyclyl, or heteroaryl, each $R^b$ is independently alkyl, fluoroalkyl, cycloalkyl, aryl, heterocyclyl, or heteroaryl, and each $R^c$ is independently a direct bond or a straight or branched alkylene, alkenylene, or alkynylene chain.

The term "hydroxyl" as used herein can refer to —OH or its ionized form, —O⁻. A "hydroxyalkyl" group is a hydroxyl-substituted alkyl group, such as HO—CH₂—. In some embodiments, the hydroxyl group may be in the form of an O-halogen group where the bond to hydrogen is replaced with a halogen. In some embodiments, the hydroxyl group may be in the form of an O-acyl group, where the bond to hydrogen is replaced with —C(O)CH₃.

The term "alkoxy" refers to hydroxyl groups (—OH) in which the bond to the hydrogen atom is replaced by a bond to a carbon atom of a substituted or unsubstituted alkyl group as defined above. Examples of linear alkoxy groups include but are not limited to methoxy, ethoxy, propoxy, butoxy, pentoxy, hexoxy, and the like. Examples of branched alkoxy groups include but are not limited to isopropxy, sec-butoxy, tert-butoxy, isopentoxy, isohexoxy, and the like. Examples of cycloalkoxy groups include but are not limited to cyclopropyloxy, cyclobutyloxy, cyclopentyloxy, cyclohexyloxy, and the like. Two subsets of alkoxy groups are "aryloxy" and "arylalkoxy," as used herein, refer to, respectively, a substituted or unsubstituted aryl group bonded to an oxygen atom and a substituted or unsubstituted aralkyl group bonded to an oxygen atom at the alkyl. Alkoxy groups may be substituted or unsubstituted. Representative substituted alkoxy groups can be substituted one or more times with substituents such as those listed above.

The term "halogen" or "halo" as used herein refers to bromine, chlorine, fluorine, or iodine. In some embodiments, the halogen is fluorine. In other embodiments, the halogen is chlorine or bromine.

The term "amine" (or "amino") as used herein refers to —NR⁷⁵R⁷⁶ and —N-G groups, wherein $R^{75}$ and $R^{76}$ are independently hydrogen, or a substituted or unsubstituted alkyl, alkenyl, alkynyl, cycloalkyl, aryl, aralkyl, heterocyclylalkyl or heterocyclyl group as defined herein. In some embodiments, the amine is alkylamino, dialkylamino, arylamino, or alkylarylamino. In other embodiments, the amine is NH₂, methylamino, dimethylamino, ethylamino, diethylamino, propylamino, isopropylamino, phenylamino, or benzylamino. G is an amine protecting group. Amine protecting groups are well known to one of ordinary skill in the art. An extensive list of protecting groups for the amine group functionality may be found in Protective Groups in Organic Synthesis, Greene, T. W.; Wuts, P. G. M., John Wiley & Sons, New York, N.Y., (3rd Edition, 1999) which can be added or removed using the procedures set forth therein and which is hereby incorporated by reference in its entirety and for any and all purposes as if fully set forth herein.

The term "imine" refers to groups of formula —CR$^{100}$=NR$^{101}$ and/or —N=CR$^{100}$R$^{101}$ groups, wherein R$^{100}$ and R$^{101}$ are each independently hydrogen or a substituted or unsubstituted alkyl, cycloalkyl, heterocyclyl, alkenyl, alkynyl, aryl, aralkyl, or heterocyclyl group as defined herein, with the proviso that R$^{100}$ and R$^{101}$ are not both simultaneously hydrogen. In any embodiment herein, "imine" also encompasses the enamine tautomer. The term "enamine" refers to —C(R$^{94}$)=C(R$^{95}$)NR$^{96}$R$^{97}$ and —NR$^{94}$C(R$^{95}$)=C(R$^{96}$)R$^{97}$, wherein R$^{94}$, R$^{95}$, R$^{96}$ and R$^{97}$ are each independently hydrogen, a substituted or unsubstituted alkyl, cycloalkyl, alkenyl, alkynyl, aryl aralkyl, heterocyclyl or heterocyclylalkyl group as defined herein.

The terms "optional" or "optionally" mean that a subsequently described event or circumstance may or may not occur and that the description includes instances when the event or circumstance occurs and instances in which it does not. For example, "optionally substituted aryl" means that the aryl radical may or may not be substituted and that the description includes both substituted aryl radicals and aryl radicals having no substitution.

The term "stereoisomers" is a general term for all isomers of individual molecules that differ only in the orientation of their atoms in space. It includes enantiomers and isomers of compounds with more than one chiral center that are not mirror images of one another (diastereomers).

As used herein, the term "tautomers" refers to particular isomers of a compound in which a hydrogen and double bond have changed position with respect to the other atoms of the molecule. Examples of tautomers include keto-enol forms, imine-enamine forms, amide-imino alcohol forms, amidine-aminidine forms, nitroso-oxime forms, thio ketone-enethiol forms, N-nitroso-hydroxyazo forms, nitro-aci-nitro forms, and pyridone-hydroxypyridine forms.

As used herein, the term "salt" of compounds disclosed herein that are within the scope of the present technology include acid or base addition salts which retain the desired pharmacological activity and are not biologically undesirable (e.g., the salt is not unduly toxic, allergenic, or irritating, and is bioavailable). When the compound of the present technology has a basic group, such as, for example, an amino group, pharmaceutically acceptable salts can be formed with inorganic acids (such as hydrochloric acid, hydroboric acid, nitric acid, sulfuric acid, and phosphoric acid), organic acids (e.g., alginate, formic acid, acetic acid, benzoic acid, gluconic acid, fumaric acid, oxalic acid, tartaric acid, lactic acid, maleic acid, citric acid, succinic acid, malic acid, methanesulfonic acid, benzenesulfonic acid, naphthalene sulfonic acid, and p-toluenesulfonic acid) or acidic amino acids (such as aspartic acid and glutamic acid). When the compound of the present technology has an acidic group, such as for example, a carboxylic acid group, it can form salts with metals, such as alkali and earth alkali metals (e.g., Na$^+$, Li$^+$, K$^+$, Ca$^{2+}$, Mg$^{2+}$, Zn$^{2+}$), ammonia or organic amines (e.g., dicyclohexylamine, trimethylamine, dimethylamine, pyridine, picoline, ethanolamine, diethanolamine, triethanolamine) or basic amino acids (e.g., arginine, lysine, and ornithine). Such salts can be prepared in situ during isolation and purification of the compounds or by separately reacting the purified compound in its free base or free acid form with a suitable acid or base, respectively, and isolating the salt thus formed.

As used herein, the term "acyloxylation" or "acyloxylating" refers to a process that introduces an acyloxy group (—OC(O)—R$^{102}$) to a carbon atom of a primary alkyl amine as described herein, where R$^{102}$ is a substituted or unsubstituted alkyl, cycloalkyl, heterocyclyl, alkenyl, alkynyl, aryl, aralkyl, or heterocyclyl group as defined herein. For example, in any embodiment herein, the acyloxylation is an acetoxylation reaction, where a —OC(O)CH$_3$ group is introduced to a carbon atom of a primary alkyl amine as described herein.

The synthesis of valuable 1,2-amino alcohols from less expensive starting materials in a safe and economical manner is described herein. Current processes of making 1,2-amino alcohols from alkanes typically require hazardous, multi-step synthetic routes involving nitration of an alkane, reaction with formaldehyde, and hydrogenation. The inventors of the present technology have discovered a process for synthesizing primary amino alcohols from primary alkyl amines, where primary amino alcohols include hydroxyl functionality at the β-position. Surprisingly, the inventors discovered that installation of a carbonyl directing group to the nitrogen of the primary alkyl amine allows for selective functionalization at the β-position. In contrast, current processes that employ similar directing groups do not exhibit selective functionalization at the β-position of primary alkyl amines or are not obtainable from primary alkyl amines. Described herein are synthetic routes to obtain 1,2 amino alcohols from primary alkyl amines, such as tert-butylamine, as primary amines tend to be inexpensive and available on a large scale.

In one aspect, a process for the preparation of an amino alcohol is provided, the process that includes: condensing a compound of Formula (II), a stereoisomer, a tautomer, or a salt thereof with a compound of Formula (IIIa) or Formula (IIIb), a stereoisomer, a tautomer, or a salt thereof to form a condensation product; hydroxylating or acyloxylating the condensation product in the presence of an oxidant to obtain a hydroxylation or acyloxylation product; and subjecting the hydroxylation or acyloxylation product to one or more subsequent reactions comprising a hydrolysis reaction, an aminolysis reaction, alcohol deprotection, or a combination thereof to obtain an amino alcohol of Formula (I); where:

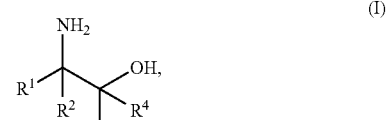

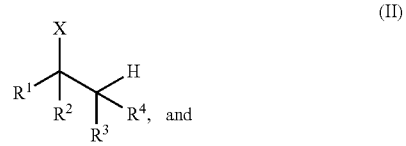

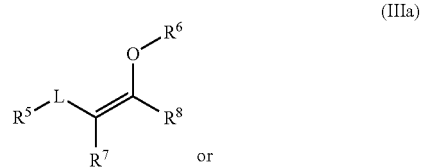

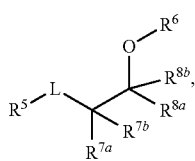

(IIIb)

L is a carbonyl, imine, acetal, or hemiacetal;
X is an amine or a protected amine;
$R^1$, $R^2$, $R^3$, and $R^4$ are each independently a hydrogen, a substituted or unsubstituted $C_1$-$C_{10}$ alkyl, a substituted or unsubstituted $C_3$-$C_{10}$ cycloalkyl, a substituted or unsubstituted aryl, a substituted or unsubstituted heterocyclyl, a substituted or unsubstituted heteroaryl, or two or more of $R^1$, $R^2$, $R^3$, and $R^4$ together with the atoms to which they are attached form a substituted or unsubstituted cycloalkyl, substituted or unsubstituted heterocyclyl, substituted or unsubstituted aromatic, or substituted or unsubstituted heteroaromatic ring;
$R^5$ is a hydrogen, halogen, a hydroxyl, an alkoxy, an O-acyl, a substituted or unsubstituted $C_1$-$C_{10}$ alkyl, a substituted or unsubstituted $C_3$-$C_{10}$ cycloalkyl, a substituted or unsubstituted aryl, a substituted or unsubstituted heterocyclyl, or a substituted or unsubstituted heteroaryl;
$R^6$ is a hydrogen, a substituted or unsubstituted $C_1$-$C_{10}$ alkyl, a substituted or unsubstituted $C_3$-$C_{10}$ cycloalkyl, a substituted or unsubstituted aryl, a substituted or unsubstituted heterocyclyl, or a substituted or unsubstituted heteroaryl;
$R^7$ and $R^8$ in Formula (IIIa) are each independently a hydrogen, a substituted or unsubstituted $C_1$-$C_{10}$ alkyl, a substituted or unsubstituted $C_3$-$C_{10}$ cycloalkyl, a substituted or unsubstituted aryl, a substituted or unsubstituted heterocyclyl, a substituted or unsubstituted heteroaryl, or $R^7$ and $R^8$ together with the atoms to which they are attached form a substituted or unsubstituted aromatic or heteroaromatic ring; and
$R^{7a}$, $R^{7b}$, $R^{8a}$, and $R^{8b}$ in Formula (IIIb) are each independently a hydrogen, a substituted or unsubstituted $C_1$-$C_{10}$ alkyl, a substituted or unsubstituted $C_3$-$C_{10}$ cycloalkyl, a substituted or unsubstituted aryl, a substituted or unsubstituted heterocyclyl, a substituted or unsubstituted heteroaryl, or two or more of $R^{7a}$, $R^{7b}$, $R^{8a}$, and $R^{8b}$ together with the atoms to which they are attached form a substituted or unsubstituted cycloalkyl or heterocyclyl ring.

In any embodiment herein, L may be a carbonyl, an imine, an acetal, or a hemiacetal. For example, in any embodiment herein, L may be a carbonyl. L may be an imine, acetal, or hemiacetal. For example, in any embodiment, L may be C=NR$^{e1}$, where R$^{e1}$ may be hydrogen, a substituted or unsubstituted $C_1$-$C_{10}$ alkyl, a substituted or unsubstituted $C_3$-$C_{10}$ cycloalkyl, a substituted or unsubstituted aryl, a substituted or unsubstituted heterocyclyl, or a substituted or unsubstituted heteroaryl. In any embodiment herein, L may be converted to a carbonyl in situ from an imine, acetal, or hemiacetal.

In any embodiment herein, X may be an amine or a protected amine. For example, in any embodiment herein, X may be an amine. The protected amine may be an amine protected with groups including, but not limited to, 9-fluorenylmethyl carbamate, t-butyl carbamate, benzyl carbamate, acetamide, trifluoroacetamide, phthalimide, triphenylmethylamine, benzylideneamine, p-toluenesulfonamide, and the like. In any embodiment herein, X may be converted from a protected amine to an amine in situ.

In any embodiment herein, $R^1$ may be a substituted or unsubstituted $C_1$-$C_6$ alkyl. For example, in any embodiment herein, $R^1$ may be selected from the group consisting of —CH$_3$, —CH$_2$CH$_2$Ph, and —CH$_2$C(CH$_3$)$_3$. In any embodiment herein, $R^2$ may be a substituted or unsubstituted $C_1$-$C_6$ alkyl. For example, in any embodiment herein, $R^2$ may be methyl. In any embodiment herein, $R^3$ and $R^4$ may independently be hydrogen or a substituted or unsubstituted $C_1$-$C_6$ alkyl. For example, in any embodiment herein, $R^3$ and $R^4$ may be hydrogen. In any embodiment herein, the compound of Formula II may include, but is not limited to, n-butyl amine, sec-butyl amine, or tert-butyl amine.

In any embodiment herein, $R^5$ and $R^6$ may each independently be hydrogen or a substituted or unsubstituted $C_1$-$C_6$ alkyl. $R^5$ and $R^6$ may be a hydrogen. $R^6$ may be a hydroxyalkyl. For example, in any embodiment herein, $R^6$ may be hydroxyethyl. $R^7$ and $R^8$ together with the atoms to which they are attached may form a $C_5$-$C_{10}$ aromatic ring. In any embodiment herein, the aromatic ring may be a substituted or unsubstituted $C_6$ aromatic ring.

$R^7$ and $R^8$ in Formula (IIIa) together with the atoms to which they are attached may form a $C_5$-$C_{10}$ aromatic ring. For example, in any embodiment herein, the aromatic ring may be a substituted or unsubstituted $C_6$ aromatic ring. In any embodiment herein, the compound of Formula (IIIa) or Formula (IIIb), a diastereomer, a tautomer, or salt thereof, may be represented by a compound of Formula (IVa) or Formula (IVb),

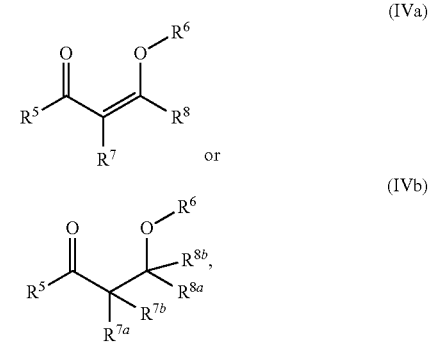

a diastereomer, a tautomer, or salt thereof. In Formulae IVa and IVb, $R^5$ is a hydrogen, halogen, a hydroxyl, an alkoxy, an O-acyl, a substituted or unsubstituted $C_1$-$C_{10}$ alkyl, a substituted or unsubstituted $C_3$-$C_{10}$ cycloalkyl, a substituted or unsubstituted aryl, a substituted or unsubstituted heterocyclyl, or a substituted or unsubstituted heteroaryl; $R^6$ is a hydrogen, a substituted or unsubstituted $C_1$-$C_{10}$ alkyl, a substituted or unsubstituted $C_3$-$C_{10}$ cycloalkyl, a substituted or unsubstituted aryl, a substituted or unsubstituted heterocyclyl, or a substituted or unsubstituted heteroaryl; $R^7$ and $R^8$ in Formula (VIa) are each independently a hydrogen, a substituted or unsubstituted $C_1$-$C_{10}$ alkyl, a substituted or unsubstituted $C_3$-$C_{10}$ cycloalkyl, a substituted or unsubstituted aryl, a substituted or unsubstituted heterocyclyl, a substituted or unsubstituted heteroaryl, or $R^7$ and $R^8$ together with the atoms to which they are attached form a substituted or unsubstituted aromatic or heteroaromatic ring; and $R^{7a}$, $R^{7b}$, $R^{8a}$, and $R^{8b}$ in Formula (VIb) are each independently a hydrogen, a substituted or unsubstituted $C_1$-$C_{10}$ alkyl, a substituted or unsubstituted $C_3$-$C_{10}$ cycloalkyl, a substituted or unsubstituted aryl, a substituted or unsubstituted heterocyclyl, a substituted or unsubstituted heteroaryl, or two or more of $R^{7a}$, $R^{7b}$, $R^{8a}$, and $R^{8b}$ together with the atoms to which they are attached form a substituted or unsubstituted cycloalkyl or heterocyclyl ring. $R^5$ and $R^6$ may each independently be hydrogen or a substituted or unsubstituted $C_1$-$C_6$ alkyl. $R^5$ and $R^6$ may be a hydrogen. $R^6$ may be a hydroxyalkyl. For example, in any embodiment herein, $R^6$ may be hydroxyethyl. $R^7$ and $R^8$ in Formula (IVa) together with the atoms to which they are attached may form a $C_5$-$C_{10}$ aromatic ring. In any embodiment herein, the aromatic ring may be a substituted or unsubstituted $C_6$ aromatic ring.

The compound of Formula (IIIa) or Formula (IVa) may, in some embodiments, be represented by a compound of Formula (V):

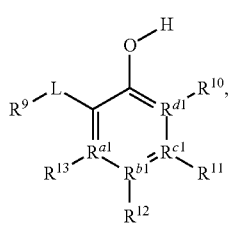

(V)

a tautomer, or a salt thereof.

In Formula V, L may be a carbonyl, an imine, an acetal, or a hemiacetal; $R^9$ may be hydrogen, hydroxyl, alkoxy, O-acyl, or O-halogen; $R^{10}$, $R^{11}$, $R^{12}$, and $R^{13}$ may each independently be a hydrogen, a halogen, an alkoxy, a substituted or unsubstituted $C_1$-$C_{10}$ alkyl, a substituted or unsubstituted $C_3$-$C_{10}$ cycloalkyl, a substituted or unsubstituted aryl, a substituted or unsubstituted heterocyclyl, a substituted or unsubstituted heteroaryl, or two or more of $R^{10}$, $R^{11}$, $R^{12}$, and $R^{13}$ together with the atoms to which they are attached form a substituted or unsubstituted cycloalkyl, substituted or unsubstituted heterocyclyl, substituted or unsubstituted aromatic, or substituted or unsubstituted heteroaromatic ring; and $R^{a1}$, $R^{b1}$, $R^{c1}$, and $R^{d1}$ are each independently a C—R', N, or N$^+$—R', where: R' is any one of $R^{10}$, $R^{11}$, $R^{12}$, or $R^{13}$; and when any one of $R^{a1}$, $R^{b1}$, $R^{c1}$, or $R^{d1}$ is N, the compound of Formula (V) does not include the corresponding $R^{10}$, $R^{11}$, $R^{12}$, and $R^{13}$ substituent. In any embodiment herein, L may be a carbonyl. In any embodiment herein, L may be an imine, acetal, or hemiacetal. For example, in any embodiment, L may be C=NR$^{e1}$, where $R^{e1}$ may be hydrogen, a substituted or unsubstituted $C_1$-$C_{10}$ alkyl, a substituted or unsubstituted $C_3$-$C_0$ cycloalkyl, a substituted or unsubstituted aryl, a substituted or unsubstituted heterocyclyl, or a substituted or unsubstituted heteroaryl. In any embodiment herein, L may be converted to a carbonyl in situ from an imine, acetal, or hemiacetal.

In any embodiment herein, $R^9$ may be hydrogen. In any embodiment herein, $R^{10}$, $R^{11}$, $R^{12}$, and $R^{13}$ may be hydrogen. For example, in any embodiment herein, $R^{10}$, $R^{11}$, $R^{12}$, and $R^{13}$ may be hydrogen, and $R^{a1}$, $R^{b1}$, $R^{c1}$, and $R^{d1}$ may be C—R'. In any embodiment herein, at least one of $R^{10}$, $R^{11}$, $R^{12}$, and $R^{13}$ may be an alkoxy, a halogen, or a $C_1$-$C_6$ alkyl. For example, in any embodiment herein, $R^9$ may be hydrogen, at least one of $R^{10}$, $R^{11}$, $R^{12}$, and $R^{13}$ may be an alkoxy, a halogen, or a $C_1$-$C_6$ alkyl; and $R^{a1}$, $R^{b1}$, $R^{c1}$, and $R^{d1}$ may be C—R'. In any embodiment herein, the compound of Formula (IIIa), Formula (IVa), or Formula (V) may be

(2-hydroxybenzaldehyde).

In any embodiment herein, the compound of Formula (IIIa), Formula (IVa), or Formula (V) may include, but is not limited to,

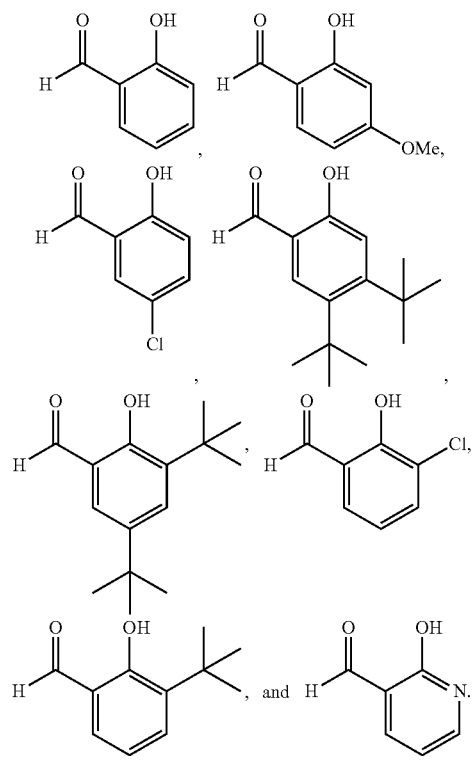

In any embodiment herein, the condensation product may include an imine, an amide, or the like or combinations thereof. In some embodiments, the condensation product may be an imine. In any embodiment herein, the condensation product may be represented by a structure of Formula (VI),

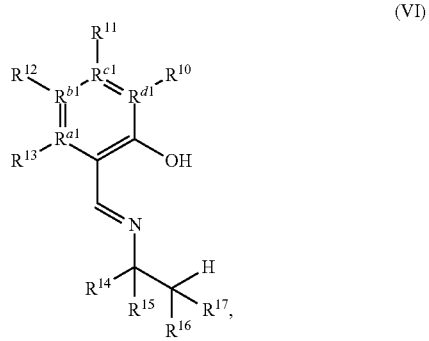

(VI)

a diastereomer, a tautomer, or a salt thereof.

In Formula VI, $R^{10}$, $R^{11}$, $R^{12}$, and $R^{13}$ may each independently be a hydrogen, a halogen, an alkoxy, a substituted or unsubstituted $C_1$-$C_{10}$ alkyl, a substituted or unsubstituted $C_3$-$C_{10}$ cycloalkyl, a substituted or unsubstituted aryl, a substituted or unsubstituted heterocyclyl, or a substituted or unsubstituted heteroaryl; and $R^{a1}$, $R^{b1}$, $R^{c1}$, and $R^{d1}$ are each independently a C—R', N, or $N^+$—R', where: R' is any one of $R^{10}$, $R^{11}$, $R^{12}$, or $R^1$; and when any one of $R^{a1}$, $R^{b1}$, $R^{c1}$, or $R^{d1}$ is N, the compound of Formula (V) does not include the corresponding $R^{10}$, $R^{11}$, $R^{12}$, and $R^{13}$ substituent. For example, in any embodiment herein, at least one of $R^{10}$, $R^{11}$, $R^{12}$, and $R^{13}$ may be a hydrogen, an alkoxy, a halogen, or a $C_1$-$C_6$ alkyl; and $R^{a1}$, $R^{b1}$, $R^{c1}$, and $R^{d1}$ may be C—R'. $R^{14}$ may be a substituted or unsubstituted $C_1$-$C_6$ alkyl. For example, in any embodiment herein, $R^{14}$ may be selected from the group consisting of —$CH_3$, —$CH_2CH_2Ph$, and —$CH_2C(CH_3)_3$. In some embodiments, $R^{15}$ may be a $C_1$-$C_3$ alkyl. For example, in any embodiment herein, $R^{15}$ may be methyl. $R^{16}$ and $R^{17}$ may each independently be hydrogen or a substituted or unsubstituted $C_1$-$C_6$ alkyl. For example, in any embodiment herein, $R^{16}$ and $R^{17}$ are hydrogen.

The process of preparing amino alcohols may include hydroxylating or acyloxylating the condensation product in the presence of an oxidant to obtain a hydroxylation or acyloxylation product. Suitable oxidants include but are not limited to $PhI(O(CO)R^{f1})_2$, $PhI(OR^{f1})_2$, $PhI(TFA)_2$, $PhIO$, 2-iodoxybenzoic acid (IBX), Dess-Martin periodinane, $M_2S_2O_8$, $R^{f1}COOI$, $R^{g1}OOR^{h1}$, or $O_2$; where $R^{f1}$ is hydrogen, a $C_1$-$C_6$ alkyl, or a substituted or unsubstituted aryl; $R^{g1}$ and $R^{h1}$ are each independently a hydrogen, a $C_1$-$C_6$ alkyl, or carboxyl group; and M is an alkali metal, such as Li, Na, or K. In any embodiment herein, the oxidant may be $PhI(O(CO)R^{f1})_2$. For example, in any embodiment herein, the oxidant is $PhI(OAc)_2$.

The oxidant may be present in an amount from about 50 mol % to about 200 mol %. For example, in any embodiment herein, suitable amounts of the oxidant may include, but are not limited to, about 50 mol %, about 60 mol %, about 70 mol %, about 80 mol %, about 90 mol %, about 100 mol %, about 110 mol %, about 120 mol %, about 130 mol %, about 140 mol %, about 150 mol %, about 160 mol %, about 170 mol %, about 180 mol %, about 190 mol %, about 200 mol %, and any range including and/or in between any two of these values. In some embodiments, the amount of oxidant may include from about 50 mol % to about 200 mol %, about 90 mol % to about 200 mol %, about 130 mol % to about 200 mol %, or about 160 mol % to about 200 mol %.

The hydroxylating or acyloxylating may be conducted in the presence of one or more co-oxidants. Suitable co-oxidants include, but are not limited to, $CuCl_2$, $CuNO_3$, or combinations thereof. In any embodiment herein, the hydroxylating or acyloxylating may further include electrochemical oxidation.

The hydroxylation or acyloxylation reaction described herein may employ a heterogeneous or homogeneous catalyst. For example, in any embodiment herein, suitable catalysts include but are not limited to palladium or a palladium salt. In any embodiment herein, the catalyst may be Pd(0) or palladium (0) complexes, such as $Pd_n(dba)_m$ (m=2 or 3; n=1 or 2), $Pd(PPh_3)_4$, or the like and combinations thereof. Suitable palladium salts include, but are not limited to, $Pd(OAc)_2$ or other palladium(II) complexes, such as $Pd(OC(O)R^{i1})_2$, $PdCl_2$, $Pd(OSO_2R^{i1})_2$, $Pd(acac)_2$, $Pd(TFA)_2$, $[Pd(allyl)Cl]_2$, or $PdCl_2(PPh_3)_2$, where $R^{i1}$ is hydrogen, halogen, or a substituted or unsubstituted alkyl. In any embodiment herein, the catalyst may be $Pd(OAc)_2$. In any embodiment herein, $Pd(OAc)_2$ may be generated in situ from Pd(0) or any of the other palladium complexes described herein.

The catalyst may be present in an amount from 0.001 mol % to about 20 mol %. For example, in any embodiment herein, the amount of catalyst present in the hydroxylation or acyloxylation reaction may include about 0.001 mol %, about 0.01 mol %, about 0.1 mol %, about 0.25 mol %, about 0.5 mol %, about 1.0 mol %, about 2 mol %, about 3 mol %, about 4 mol %, about 5 mol %, about 6 mol %, about 7 mol %, about 8 mol %, about 9 mol %, about 10 mol %, about 11 mol %, about 12 mol %, about 13 mol %, about 14 mol %, about 15 mol %, about 16 mol %, about 17 mol %, about 18 mol %, about 19 mol %, about 20 mol %, and any range including and/or in between any two of these values.

Additional reactants in the hydroxylation or acyloxylation reaction may include one or more ligands or bases. In any embodiment herein, the hydroxylation or acyloxylation reaction may employ one or more ligands. Suitable ligands include, but are not limited to, one or more of

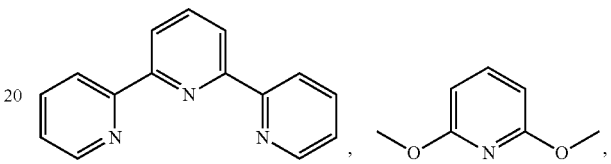

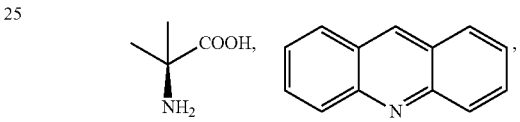

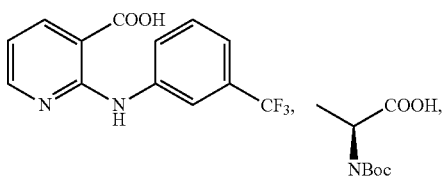

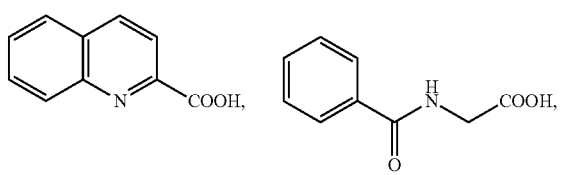

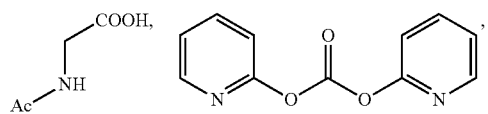

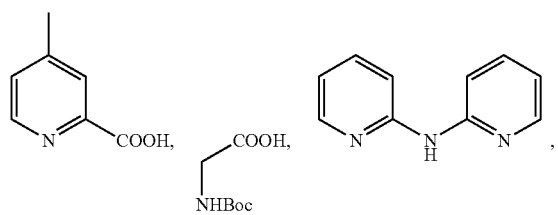

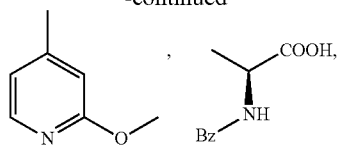

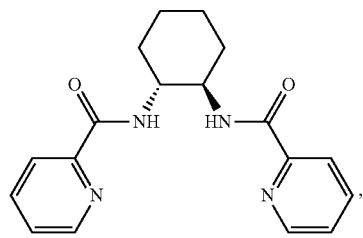

or combinations of two or more thereof. In some embodiments, the one or more ligands include an amino acid. The ligand may be present in an amount from about 0.1 mol % to about 10 mol %. Suitable amounts of ligand may include, but are not limited to, about 0.1 mol %, about 0.5 mol %, about 1 mol %, about 2 mol %, about 3 mol %, about 4 mol %, about 5 mol %, about 6 mol %, about 7 mol %, about 8 mol %, about 9 mol %, about 10 mol, and any range including and/or in between any two of these values.

In any embodiment herein, the hydroxylation or acyloxylation reaction may employ a base. Suitable bases include, but are not limited to, NaOAc, KOAc, LiOAc, $Na_2CO_3$, $NaHCO_3$, NaHPO4, $NaOS(O)_2Ph$, $NaOCOCF_3$, $NaOCOCF_2Cl$, NaOPiv, $KH_2PO_4$, $K_3PO_4$, or a combination of two or more thereof. The base may be present in an amount from about 0.01 to about 2.0 molar equivalents. For example, in any embodiment herein, the amount of base may be about 0.01, about 0.1, about 0.2, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about, 1.9, about 2.0, and any range including and/or in between any two of these values.

The hydroxylation or acyloxylation reaction may employ a solvent. Suitable solvents may include, but are not limited to, aprotic solvents. Aprotic solvents as used herein include, but are not limited to, a carbonate, a halogenated solvent, an ether, an ester, a ketone, a tertiary amide, a nitrile, a sulfoxide, a sulfone, or a mixture of any two or more thereof. For example, in any embodiment herein, the aprotic solvent may include toluene, tetrahydrofuran (THF), dioxane, dimethylformamide (DMF), dimethylsulfoxide (DMSO), m-xylene, cyclohexane, ethyl acetate, $Cl(CH_2)_2Cl$, acetonitrile, N,N'-dimethylpropyleneurea (DMPU), chloroform ($CHCl_3$), N-methylpyrrolidone, benzene, dichlorobenzene, chlorobenzene, fluorobenzene, difluorobenzene, glymes (e.g., diethylene glycol dimethyl ether, dipropylene glycol dimethyl ether, polyglyme, or the like), or a mixture of any two or more such solvents.

The hydroxylation or acyloxylation reaction may occur at a temperature from about 50° C. to about 180° C. Suitable temperatures include, but are not limited to, about 50° C. to about 180° C., about 55° C. to about 160° C., about 65° C. to about 150° C., about 70° C. to about 140° C., about 75° C. to about 130° C., about 80° C. to about 120° C., and any range including and/or in between any two of these values. In some embodiments, the temperature may be about 80° C. to about 120° C.

The processes described herein may include at least one or more subsequent reactions that include a hydrolysis reaction, an aminolysis reaction alcohol deprotection, or combinations or two or more thereof with the hydroxylation or acyloxylation product. In any embodiment herein, the hydroxylation or acyloxylation product may undergo an aminolysis reaction. For example, in any embodiment, the aminolysis may be a transimination with an amine compound, such as an amine compound of Formula II. In any embodiment herein, the alcohol deprotection may occur under basic conditions, under acidic conditions, by way of transesterification with another alcohol, such as the compound of Formula I.

The processes described herein may be carried out in several steps (sequentially) or in one step (simultaneously). For example, in any embodiment herein, the process may be carried out sequentially where the condensation reaction occurs separately from the hydroxylation or acyloxylation reaction and one or more subsequent reactions as described herein in any embodiment. In any embodiment herein, the process may be carried out simultaneously where the condensation reaction, hydroxylation or acyloxylation reaction, and one or more subsequent reactions are carried out in a one-pot reaction.

In any embodiment herein, the process may be conducted in a batch mode operation, in a fed-batch mode of operation, in continuous mode of operation, or the like. In some embodiments, the process may be conducted in fed-batch mode where reaction materials are continuously fed to a solution of the catalyst in a reaction vessel. In some embodiments, the process may be conducted in continuous mode in which all reactants and catalyst are continuously fed to a reaction vessel with or without recycling of parts of the reaction mass.

The present technology, thus generally described, will be understood more readily by reference to the following examples, which are provided by way of illustration and are not intended to be limiting of the present invention.

EXAMPLES

Example 1: General Synthesis Procedure

Scheme 1

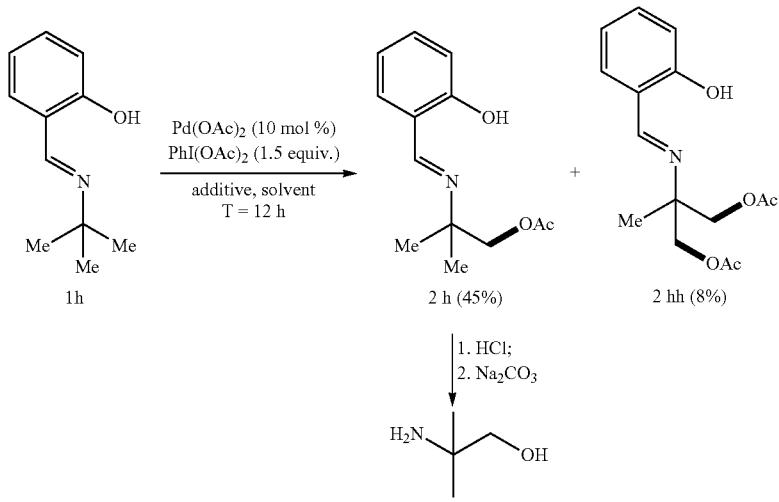

In a nitrogen-filled glove-box, Pd(OAc)$_2$ (2.2 mg), PhI(OAc)$_2$ (48 mg, 1.5 equivalents), and an additive (1.5 equiv. of base or 10 mol % of ligand) were added to a 4 mL vial with a magnetic stirrer bar, followed by solvent (1.0 mL) and compound 1h (17.7 mg). The vial was capped and stirred at 80° C. for 12 hours. The reaction mixture was diluted with ethyl acetate (2 mL), and a specific amount of dodecane was added as an internal standard. The yield of the reaction was determined by GC. [$^1$H NMR data for 2h: $^1$H NMR (500 MHz, Chloroform-d) δ 8.38 (s, 1H), 7.36-7.27 (m, 2H), 6.96 (d, J=8.2 Hz, 1H), 6.88 (td, J=7.6, 1.2 Hz, 1H), 4.11 (s, 2H), 2.07 (s, 3H), 1.35 (s, 6H); $^{13}$C NMR data for 2h: $^{13}$C NMR (176 MHz, CDCl$_3$) δ 170.91, 161.73, 161.32, 132.33, 131.57, 118.85, 118.49, 117.17, 71.29, 59.08, 24.23, 20.87. $^1$H NMR data for 2hh: $^1$H NMR (500 MHz, Chloroform-d) δ 8.44 (s, 1H), 7.35 (ddd, J=8.4, 7.2, 1.6 Hz, 1H), 7.30 (dd, J=7.6, 1.6 Hz, 1H), 6.99 (d, J=8.4 Hz, 1H), 6.91 (td, J=7.6, 1.2 Hz, 1H), 4.25 (d, J=11.2 Hz, 2H), 4.19 (d, J=11.2 Hz, 2H), 2.09 (s, 6H), 1.38 (s, 3H). $^{13}$C NMR data for 2hh: $^{13}$C NMR (176 MHz, CDCl$_3$) δ 170.65, 163.73, 161.09, 132.80, 131.92, 118.73, 117.23, 67.25, 61.19, 20.82, 18.71. Compound 2h was reacted with 0.1 mL HCl (12 M) and 0.1 mL of H$_2$O at 80° C. overnight to cleave the imine linkage of the 2-(iminomethyl)phenol directing group followed by treatment with Na$_2$CO$_3$ to remove the acetyl protecting group. D$_2$O (1.0 mL) was added to the reaction mixture, and the aqueous phase was extracted with deuterated chloroform (1.0 mL). After separation, 2-amino-2-methylpropanol was observed in the aqueous layer by $^1$H NMR. [$^1$H NMR, 500 MHz, D$_2$O]: δ 3.59 (s, 2H), 1.34 (s, 6H).

Example 2: Preparation of Acetoxylation Product with Varying Directing Groups Following the general synthesis procedure described in Example 1, mono- and di-acetoxylated 2-amino-2-methylpropyl alcohols having a substituted or unsubstituted 2-(iminomethyl)phenol directing group were prepared. Yields for the resulting products refer to $^1$HNMR yields. The substituted products were determined by comparison with the unsubstituted product, and the yields of the substituted products were determined by crude $^1$H-NMR spectrum using 1,3,5-trimethoxy benzene as internal standard.

Scheme 2

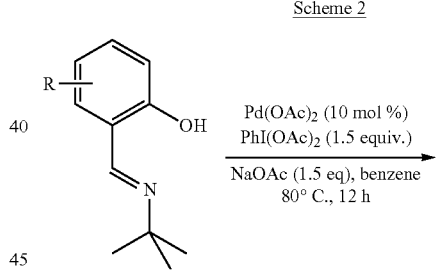

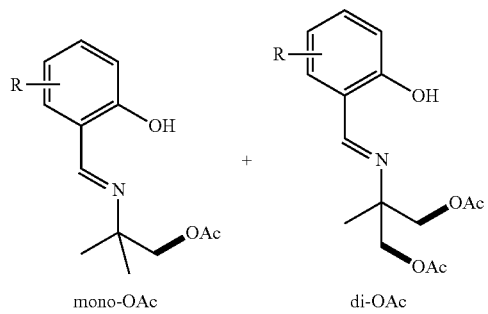

mono-OAc     di-OAc

TABLE 1

| Starting Material | SM % | mono % | di % |
|---|---|---|---|
| (1h) [2-((tert-butylimino)methyl)phenol] | 20 | 30 | 5 |
| [4-OMe salicylaldimine tBu] | 28 | 18 | 4 |
| [4-Cl salicylaldimine tBu] | 20 | 19 | 2 |
| [4,5-di-tBu salicylaldimine tBu] | 14 | 22 | 6 |
| [3,5-di-tBu salicylaldimine tBu] | 8 | 10 | 19 |

Example 3: Evaluation of Sequential C—H Functionalizations and β C—H Functionalization The following mono-, di-, and tri-acetoxylated amino alcohols having a 2-(iminomethyl)phenol directing group were prepared as illustrated in Scheme 3.

Scheme 3

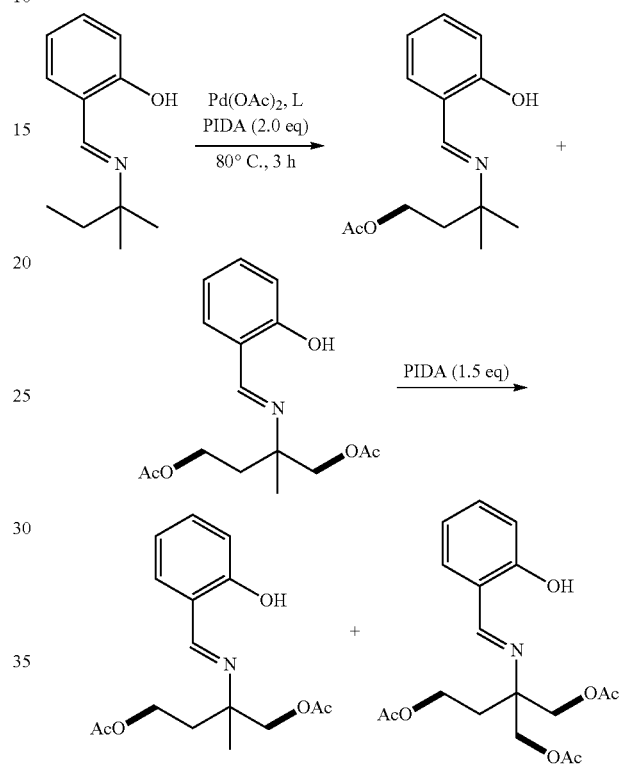

In a nitrogen-filled glove-box, Pd(OAc)$_2$ (2.2 mg), PhI(OAc)$_2$ (64 mg, 2.0 equivalents), and ligand (1.9 mg, 10 mol %) were added to a 4 mL vial with a magnetic stirrer bar, followed by solvent (1.0 mL) and imine substrate (19.1 mg). The vial was capped and stirred at 80° C. for 4 hours. Mono-OAc product and di-OAc product were observed by GC/MS. To the reaction mixture was added PhI(OAc)$_2$ (48 mg, 1.5 equivalents), and the resulting mixture was stirred overnight. GC/MS showed that mono-OAc product was completely consumed, and di-OAc product and tri-OAc product were observed. $^1$H NMR for the mono-OAc (500 MHz, Chloroform-d): δ 8.38 (s, 1H), 7.39-7.26 (m, 2H), 6.98 (d, J=8.2 Hz, 1H), 6.91 (t, J=7.4 Hz, 1H), 4.19 (t, J=7.0 Hz, 3H), 2.10-1.95 (m, 2H), 2.03 (s, 3H), 1.39 (s, 6H).

Example 4: β C—H Acetoxylation with Varying a Carbon Substituents

The following mono-acetoxylated amino alcohols having a 2-(iminomethyl)phenol directing group and varying a carbon substituents were prepared as illustrated in Scheme 4.

Scheme 4

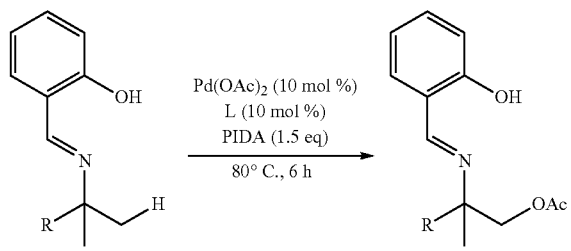

TABLE 2

| R— | SM % | mono % | di % |
|---|---|---|---|
| BnO—CH$_2$— | 34 | 6 | 25 |
| $^t$Bu—CH$_2$— | 30 | 32 | 9 |
| Ph—CH$_2$— | 34 | 28 | — |
| cyclohexyl-C(Me)$_2$— | 39 | 38 | — |

C—H acetoxylation (R=$^t$Bu-CH$_2$—)

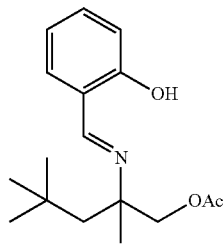 [SMILES: CC(=O)OCC(C)(CC(C)(C)C)/N=C/c1ccccc1O]

Following the general procedure for the C—H acetoxylation described in Example 1, the acetoxylated product was obtained. $^1$H NMR (500 MHz, CDCl$_3$) δ 13.92 (s, 1H), 8.40 (s, 1H), 7.37 (d, J=7.4 Hz, 1H), 7.33 (d, J=8.2 Hz, 1H), 7.00 (d, J=8.2 Hz, 1H), 6.93 (t, J=7.4 Hz, 1H), 4.14 (s, 2H), 2.10 (s, 3H), 1.88 (d, J=14.6 Hz, 1H), 1.70 (d, J=14.6 Hz, 1H), 1.48 (s, 3H), 1.01 (s, 9H); $^{13}$C NMR (176 MHz, CDCl$_3$) δ 170.8, 161.8, 161.4, 132.3, 132.3, 131.6, 131.6, 118.9, 71.3, 62.7, 51.6, 31.8, 31.8, 21.6, 21.4.

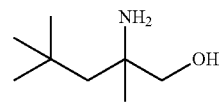

The acetoxylated product was reacted with 0.1 mL HCl (12 M) and 0.1 mL of H$_2$O at 80° C. overnight. To the reaction mixture D$_2$O (1.0 mL) and CDCl$_3$ (1.0 mL) were added. After organic layer was separated, the aqueous layer was basified with Na$_2$CO$_3$, and extracted with CDCl$_3$ (1.0 mL). 1H NMR of the organic layer was conducted. $^1$H NMR (500 MHz, Chloroform-d) δ 3.32 (s, 2H), 1.45 (s, 2H), 1.23 (s, 3H), 1.08 (s, 9H).

C—H acetoxylation (R=BnO—CH$_2$—)

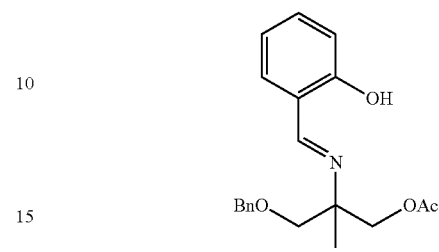

Following the general procedure for the C—H acetoxylation (Example 1), the acetoxylated product was obtained. $^1$H NMR (400 MHz, CDCl$_3$) δ 13.65 (s, 1H), 8.46 (s, 1H), 7.43-7.23 (m, 7H), 6.96 (dd, J=8.4, 1.2 Hz, 1H), 6.89 (td, J=7.6, 1.2 Hz, 1H), 4.54 (s, 2H), 4.26 (d, J=1.4 Hz, 2H), 3.61 (d, J=9.2 Hz, 1H), 3.49 (d, J=9.2 Hz, 1H), 2.05 (s, 3H), 1.37 (s, 3H); $^{13}$C NMR (176 MHz, CDCl$_3$) δ 170.8, 163.5, 161.3, 137.9, 132.4, 131.8, 128.4, 127.7, 127.6, 118.9, 118.5, 117.2, 73.7, 73.5, 67.7, 62.1, 20.8, 19.1.

Example 5: Evaluation of Ligand Effects

Following the general synthesis procedure described in Example 1, the mono- (2h) and di-acetoxylated (2hh) 2-amino-2-methylpropyl alcohols having a 2-(iminomethyl) phenol directing group were prepared using various ligands (Table 3) in the reaction mixture. Yields were determined using gas chromatography.

Scheme 5

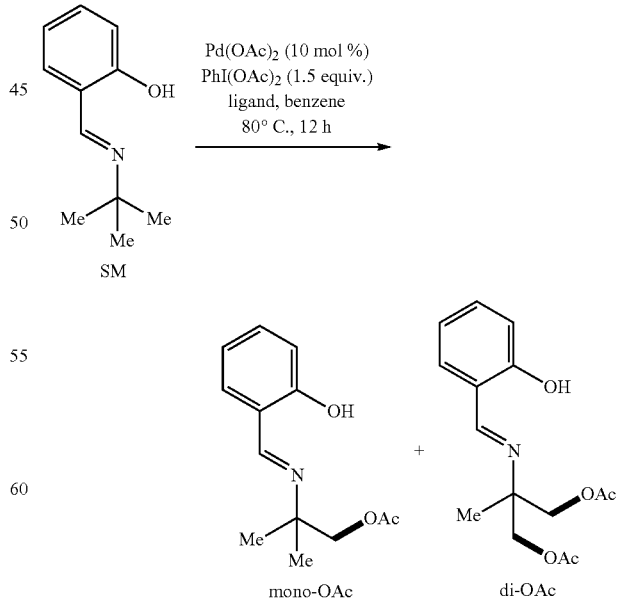

TABLE 3

| Ligand | SM % | mono % | di % |
| --- | --- | --- | --- |
| No Ligand | 18 | 39 | 9 |
| 2,2':6',2''-terpyridine | 58 | 7 | 0 |
| (1R,2R)-N,N'-bis(pyridine-2-carbonyl)cyclohexane-1,2-diamine | 44 | 20 | 2 |
| Acridine | 22 | 46 | 11 |
| Di(pyridin-2-yl) carbonate | 19 | 28 | 8 |
| Di(pyridin-2-yl)amine | 50 | 14 | 1 |
| 2,6-dimethoxypyridine | 20 | 45 | 12 |
| 2-methoxy-4-methylpyridine | 21 | 43 | 11 |
| Picolinic acid (pyridine-2-carboxylic acid) | 39 | 27 | 3 |
| Quinoline-2-carboxylic acid | 47 | 20 | 3 |
| 2-((3-(trifluoromethyl)phenyl)amino)nicotinic acid | 29 | 44 | 8 |
| N-benzoylglycine (hippuric acid) | 23 | 46 | 9 |
| Boc-Val-OH | 29 | 45 | 8 |
| Boc-Ala-OH | 23 | 41 | 10 |
| Boc-Gly-OH | 21 | 42 | 9 |
| 2-methylalanine (α-aminoisobutyric acid) | 27 | 41 | 8 |
| N-benzoyl-L-alanine | 20 | 43 | 10 |

Example 6: Evaluation of Reaction Using Various Catalyst Loadings, Temperatures, Solvents, and Bases Following the general synthesis procedure described in Example 1, the mono- (2h) and di-acetoxylated (2hh) 2-amino-2-methylpropyl alcohols having a 2-(iminomethyl) phenol directing group were prepared using various catalyst loading amounts (Table 4), temperatures (Table 5), solvents (Table 6), and bases (Table 7). Yields were determined using gas chromatography.

TABLE 4

Reaction with varying catalyst loadings.

| Catalyst Amount (mol %) | SM % | mono % | di % | Mass balance | conv. % | mono-selectivity |
| --- | --- | --- | --- | --- | --- | --- |
| 10 | 24 | 44 | 11 | 79 | 76 | 4:1 |
| 5.0 | 26 | 39 | 9 | 74 | 74 | 4:1 |
| 2.5 | 35 | 27 | 2 | 64 | 65 | 14:1 |
| 1.0 | 40 | 15 | 0 | 55 | 60 | 1:0 |
| 0.5 | 49 | 8 | 0 | 56 | 51 | 1:0 |

Mass balance = SM % + mono % + di %
conv. % = 100-SM %
mono-selectivity = mono %/di %

TABLE 5

Reaction at various temperatures

| Temperature | SM % | mono % | di % | Mass balance | conv. % | mono-selectivity |
|---|---|---|---|---|---|---|
| 120 | 30 | 9 | 0.3 | 39 | 22 | 25 |
| 100 | 27 | 30 | 2.9 | 59 | 50 | 10 |
| 80 | 32 | 31 | 2.9 | 66 | 47 | 11 |
| 65 | 50 | 7 | 0 | 57 | 12 | — |

Mass balance = SM % + mono % + di % conv. % = 100-SM % mono-selectivity = mono %/di %

TABLE 6

Reaction using various solvents.

| Solvent | SM % | mono % | di % | Mass balance | conv. % | mono-selectivity |
|---|---|---|---|---|---|---|
| toluene | 32 | 31 | 2.9 | 66 | 47 | 11 |
| THF | 62 | 7 | 0 | 68 | 10 | — |
| dioxane | 33 | 14 | 0 | 47 | 30 | 14 |
| DMF | 41 | 4 | 0 | 45 | 8 | — |
| DMSO | 30 | 1.8 | 0 | 32 | 6 | — |
| m-xylene | 15 | 30 | 4 | 49 | 61 | 8 |
| cyclohexane | 43 | 8 | 0 | 51 | 16 | — |
| ethyl acetate | 26 | 25 | 3 | 53 | 46 | 8 |
| $Cl(CH_2)_2Cl$ | 13 | 40 | 12 | 64 | 62 | 3 |
| acetonitrile | 28 | 22 | 3 | 52 | 50 | 8 |
| DMPU | 79 | 0 | 0 | 79 | 0 | — |
| $CHCl_3$ | 10 | 33 | 15 | 58 | 57 | — |
| benzene | 13 | 41 | 10 | 64 | 64 | 4 |

Mass balance = SM % + mono % + di % conv. % = 100-SM % mono-selectivity = mono %/di %

TABLE 7

Reaction using various bases.

| Base | SM % | mono % | di % | Mass balance | conv. % | mono-selectivity |
|---|---|---|---|---|---|---|
| NaOAc | 32 | 31 | 2.9 | 66 | 47 | 11 |
| KOAc | 42 | 18 | 1 | 61 | 31 | 18 |
| LiOAc | 30 | 14 | 1 | 45 | 33 | 14 |
| $Na_2CO_3$ | 60 | 1 | 0 | 61 | 2 | — |
| $Na_2HPO_4$ | 17 | 41 | 9 | 67 | 75 | 5 |
| $NaOS(O)_2Ph$ | 16 | 42 | 10 | 67 | 78 | 5 |
| $NaOCOCF_3$ | 30 | 5 | 1 | 36 | 17 | 5 |
| $NaOCOCF_2Cl$ | 23 | 3 | 1 | 27 | 15 | 3 |
| NaOPiv | 39 | 2 | 1 | 42 | 7 | 2 |
| $KH_2PO_4$ | 16 | 41 | 8 | 65 | 75 | 5 |
| $K_3PO_4$ | 35 | 18 | 1 | 54 | 35 | 18 |

OAc is acetate

Mass balance = SM % + mono % + di % conv. % = 100-SM % mono-selectivity = mono %/di %

Example 7: Synthesis of Imine, General Procedure

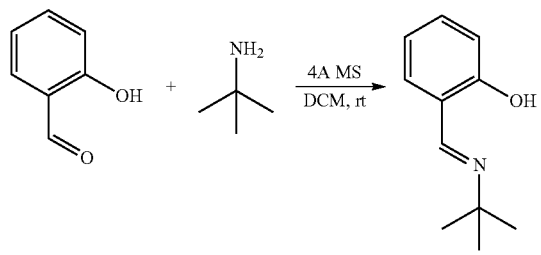

To a 20 mL vial were added salicylaldehyde (1.2 g, 10 mmol), dichloromethane ("DCM;" 10 mL), 4 Å molecular sieves ("4 A MS;" 1.0 g), and tert-butyl amine (0.77 g, 10.5 mmol). The reaction mixture was stirred at room temperature for 2 hours, after which time the reaction mixture was filtered through a short pad of Celite, and washed with additional DCM (2 mL). The filtrate was evaporated to remove volatiles to yield the product as a light yellow liquid (1.6 g, 90%). $^1$H NMR (500 MHz, CDCl$_3$) δ 14.45 (s, 1H), 8.36 (s, 1H), 7.32 (t, J=7.8 Hz, 1H), 7.28 (d, J=7.4 Hz, 2H), 6.97 (d, J=8.2 Hz, 1H), 6.88 (s, 7.8H), 1.37 (s, 9H).

Example 8: Synthesis of an Acetoxylation Product

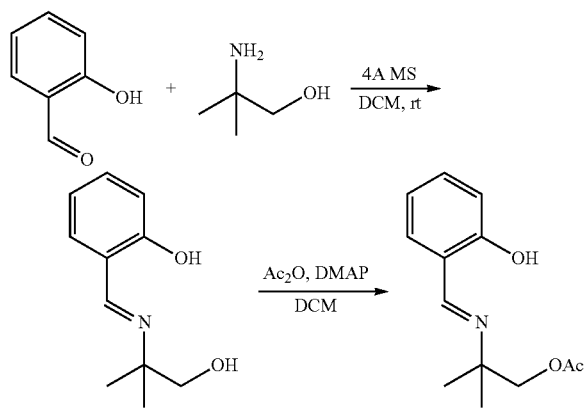

A synthetic process independent from the process of the present technology was carried out to confirm the structure of the acetoxylation product. To a 20 mL vial were added salicylaldehyde (2.4 g, 20 mmol), DCM (10 mL), 4 A MS (2.0 g), and 2-amino-2-methyl propanol (1.8 g, 20 mmol). The reaction mixture was stirred at room temperature for 1 hour, after which time the reaction mixture was filtered through a short pad of Celite, and washed with DCM (2 mL). The filtrate was evaporated to remove volatiles and yield the product imine as a light yellow liquid.

The crude imine product was used in the following step directly. To a 20 mL vial were added the imine (0.32 g, 1.7 mmol), DCM (5 mL), acetic anhydride (0.19 g, 1.8 mmol), and dimethylaminopyridine ("DMAP;" 0.23 g, 1.9 mmol). The reaction mixture was stirred at room temperature for 3 hours, after which time the reaction mixture was diluted with DCM (10 mL), and then washed with water (30 mL, twice), diluted aqueous HCl (5 mL) and brine (10 mL). The organic layer was dried over Na$_2$SO$_4$, filtered, and condensed under reduced pressure to give the product 2h (see Example 1) as a light yellow oil. $^1$H NMR (500 MHz, Chloroform-d) δ 8.38 (s, 1H), 7.36-7.27 (m, 2H), 6.96 (d, J=8.2 Hz, 1H), 6.88 (td, J=7.6, 1.2 Hz, 1H), 4.11 (s, 2H), 2.07 (s, 3H), 1.35 (s, 6H); $^{13}$C NMR (176 MHz, CDCl$_3$) δ 170.91, 161.73, 161.32, 132.33, 131.57, 118.85, 118.49, 117.17, 71.29, 59.08, 24.23, 20.87.

Example 9: Synthesis of a Di-Acetoxylation Product

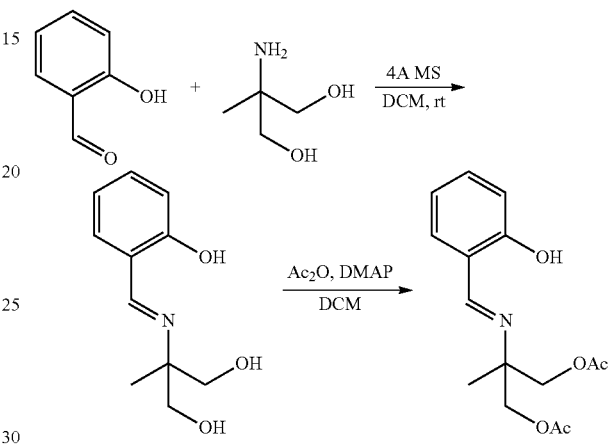

A synthetic process independent from the process of the present technology was carried out to confirm the structure of the acetoxylation product. To a 20 mL vial were added salicylaldehyde (1.2 g, 10 mmol), DCM (50 mL), 4 A MS (2.0 g), and 2-amino-2-methylpropane-1,3-diol (1.1 g, 10 mmol). The reaction mixture was stirred at room temperature for 3 hours, after which time the reaction mixture was filtered through a short pad of Celite, and washed with DCM (2 mL). The filtrate was evaporated to remove volatiles to yield the product imine as a light yellow liquid. The imine was used in the following step directly.

To a 20 mL vial were added the imine (0.42 g, 2.0 mmol), DCM (5 mL), acetic anhydride (0.45 g, 4.4 mmol), and DMAP (0.56 g, 4.6 mmol). The reaction mixture was stirred at room temperature for 3 hours, after which time the reaction mixture was diluted with DCM (10 mL), and then was washed with water (30 mL, twice), diluted aqueous HCl (5 mL) and brine (10 mL). The organic layer was dried over Na$_2$SO$_4$, filtered, and condensed under reduced pressure to give the product 2hh as a light yellow oil. $^1$H NMR (500 MHz, Chloroform-d) δ 8.44 (s, 1H), 7.35 (ddd, J=8.4, 7.2, 1.6 Hz, 1H), 7.30 (dd, J=7.6, 1.6 Hz, 1H), 6.99 (d, J=8.4 Hz, 1H), 6.91 (td, J=7.6, 1.2 Hz, 1H), 4.25 (d, J=11.2 Hz, 2H), 4.19 (d, J=11.2 Hz, 2H), 2.09 (s, 6H), 1.38 (s, 3H). $^{13}$C NMR (176 MHz, CDCl$_3$) δ 170.65, 163.73, 161.09, 132.80, 131.92, 118.73, 117.23, 67.25, 61.19, 20.82, 18.71.

Example 10: Other Salicylaldehydes

Following the general synthesis procedure described in Example 1, mono- and di-acetoxylated 2-amino-2-methylpropyl alcohols having a substituted or unsubstituted 2-(iminomethyl)phenol directing group were prepared. Yields for the resulting products refer to $^1$H NMR yields. The substituted products were determined by comparison with the unsubstituted product, and the yields of the substituted products were determined by crude $^1$H NMR spectrum using 1,3,5-trimethoxy benzene as internal standard.

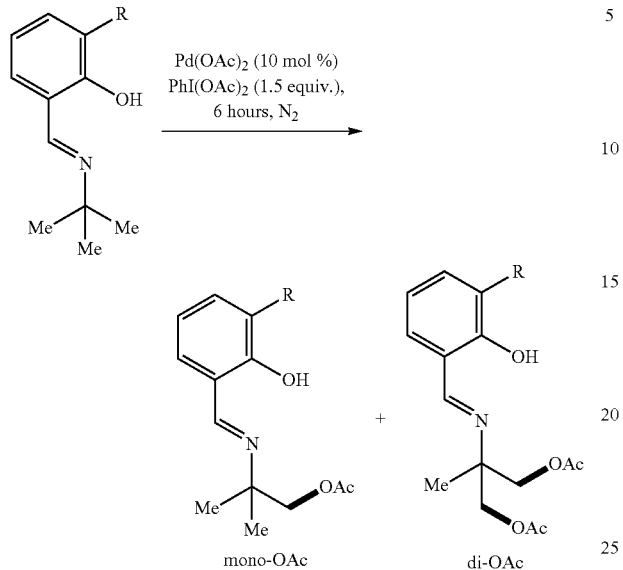

| R | SM % | mono % | di % |
| --- | --- | --- | --- |
| — | 26 | 32 | 7 |
| tBu | 45 | 21 | 4 |
| Cl | 33 | 17 | 2 |

Para. 1. In one aspect, a process for the preparation of an amino alcohol is provided, the process comprising:

condensing a compound of Formula (II), a stereoisomer, a tautomer, or a salt thereof with a compound of Formula (IIIa) or Formula (IIIb), a stereoisomer, a tautomer, or a salt thereof to form a condensation product;

hydroxylating or acyloxylating the condensation product in the presence of an oxidant to obtain a hydroxylation or acyloxylation product; and subjecting the hydroxylation or acyloxylation product to one or more subsequent reactions comprising a hydrolysis reaction, an aminolysis reaction, alcohol deprotection, or a combination of two or more thereof to obtain an amino alcohol of Formula (I);

wherein:

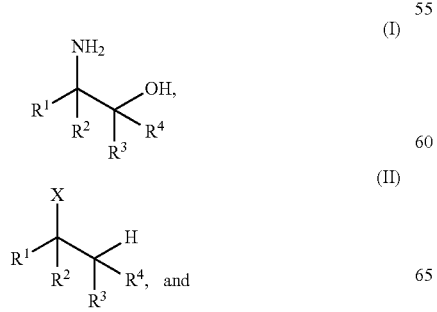

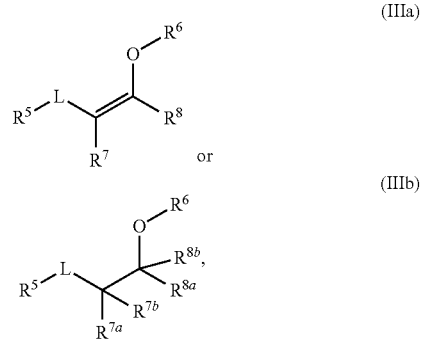

L is a carbonyl, imine, acetal, or hemiacetal;

X is an amine or a protected amine;

$R^1$, $R^2$, $R^3$, and $R^4$ are each independently a hydrogen, a substituted or unsubstituted $C_1$-$C_{10}$ alkyl, a substituted or unsubstituted $C_3$-$C_{10}$ cycloalkyl, a substituted or unsubstituted aryl, a substituted or unsubstituted heterocyclyl, a substituted or unsubstituted heteroaryl, or two or more of $R^1$, $R^2$, $R^3$, and $R^4$ together with the atoms to which they are attached form a substituted or unsubstituted cycloalkyl, substituted or unsubstituted heterocyclyl, substituted or unsubstituted aromatic, or substituted or unsubstituted heteroaromatic ring;

$R^5$ is a hydrogen, a halogen, a hydroxyl, an alkoxy, an O-acyl, a substituted or unsubstituted $C_1$-$C_{10}$ alkyl, a substituted or unsubstituted $C_3$-$C_{10}$ cycloalkyl, a substituted or unsubstituted aryl, a substituted or unsubstituted heterocyclyl, or a substituted or unsubstituted heteroaryl;

$R^6$ is a hydrogen, a substituted or unsubstituted $C_1$-$C_{10}$ alkyl, a substituted or unsubstituted $C_3$-$C_{10}$ cycloalkyl, a substituted or unsubstituted aryl, a substituted or unsubstituted heterocyclyl, or a substituted or unsubstituted heteroaryl;

$R^7$ and $R^8$ in Formula (IIIa) are each independently a hydrogen, a substituted or unsubstituted $C_1$-$C_{10}$ alkyl, a substituted or unsubstituted $C_3$-$C_{10}$ cycloalkyl, a substituted or unsubstituted aryl, a substituted or unsubstituted heterocyclyl, a substituted or unsubstituted heteroaryl, or $R^7$ and $R^8$ together with the atoms to which they are attached form a substituted or unsubstituted aromatic or heteroaromatic ring; and $R^{7a}$, $R^{7b}$, $R^{8a}$, and $R^{8b}$ in Formula (IIIb) are each independently a hydrogen, a substituted or unsubstituted $C_1$-$C_{10}$ alkyl, a substituted or unsubstituted $C_3$-$C_{10}$ cycloalkyl, a substituted or unsubstituted aryl, a substituted or unsubstituted heterocyclyl, a substituted or unsubstituted heteroaryl, or two or more of $R^{7a}$, $R^{7b}$, $R^{8a}$, and $R^{8b}$ together with the atoms to which they are attached form a substituted or unsubstituted cycloalkyl or heterocyclyl ring.

Para. 2. In another aspect, a process for the preparation of an amino alcohol is provided, the process comprising:

condensing a compound of Formula (II), a stereoisomer, a tautomer, or a salt thereof with a compound of Formula (IVa) or Formula (IVb), a stereoisomer, a tautomer, or a salt thereof to form a condensation product;

hydroxylating or acyloxylating the condensation product in the presence of an oxidant to obtain a hydroxylation or acyloxylation product; and subjecting the hydroxylation or acyloxylation product to one or more subsequent reactions comprising a hydrolysis reaction, an aminolysis reaction, alcohol deprotection, or a combination of two or more thereof to obtain an amino alcohol of Formula (I);
wherein:

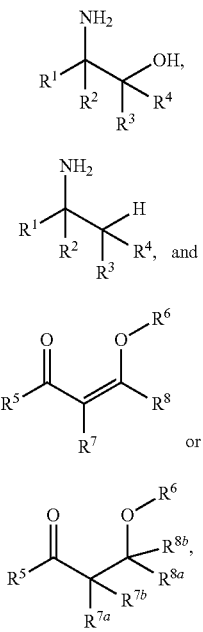

(I), (II), (IVa) or (IVb)

$R^1$, $R^2$, $R^3$, and $R^4$ are each independently a hydrogen, a substituted or unsubstituted $C_1$-$C_{10}$ alkyl, a substituted or unsubstituted $C_3$-$C_{10}$ cycloalkyl, a substituted or unsubstituted aryl, a substituted or unsubstituted heterocyclyl, a substituted or unsubstituted heteroaryl, or two or more of $R^1$, $R^2$, $R^3$, and $R^4$ together with the atoms to which they are attached form a substituted or unsubstituted cycloalkyl, substituted or unsubstituted heterocyclyl, substituted or unsubstituted aromatic, or substituted or unsubstituted heteroaromatic ring;

$R^5$ is a hydrogen, a halogen, a hydroxyl, an alkoxy, an O-acyl, a substituted or unsubstituted $C_1$-$C_{10}$ alkyl, a substituted or unsubstituted $C_3$-$C_{10}$ cycloalkyl, a substituted or unsubstituted aryl, a substituted or unsubstituted heterocyclyl, or a substituted or unsubstituted heteroaryl;

$R^6$ is a hydrogen, a substituted or unsubstituted $C_1$-$C_{10}$ alkyl, a substituted or unsubstituted $C_3$-$C_{10}$ cycloalkyl, a substituted or unsubstituted aryl, a substituted or unsubstituted heterocyclyl, or a substituted or unsubstituted heteroaryl;

$R^7$ and $R^8$ in Formula (IIIa) are each independently a hydrogen, a substituted or unsubstituted $C_1$-$C_{10}$ alkyl, a substituted or unsubstituted $C_3$-$C_{10}$ cycloalkyl, a substituted or unsubstituted aryl, a substituted or unsubstituted heterocyclyl, a substituted or unsubstituted heteroaryl, or $R^7$ and $R^8$ together with the atoms to which they are attached form a substituted or unsubstituted aromatic or heteroaromatic ring; and $R^{7a}$, $R^{7b}$, $R^{8a}$, and $R^{8b}$ in Formula (IIIb) are each independently a hydrogen, a substituted or unsubstituted $C_1$-$C_{10}$ alkyl, a substituted or unsubstituted $C_3$-$C_{10}$ cycloalkyl, a substituted or unsubstituted aryl, a substituted or unsubstituted heterocyclyl, a substituted or unsubstituted heteroaryl, or two or more of $R^{7a}$, $R^{7b}$, $R^{8a}$, and $R^{8b}$ together with the atoms to which they are attached form a substituted or unsubstituted cycloalkyl or heterocyclyl ring.

Para. 3. The process of Para. 1 or 2, wherein $R^1$ is a substituted or unsubstituted $C_1$-$C_6$ alkyl.

Para. 4. The process of Para. 3, wherein $R^1$ is selected from the group consisting of —$CH_3$, —$CH_2CH_2Ph$, and —$CH_2C(CH_3)_3$.

Para. 5. The process of any one of Paras. 1-4, wherein $R^2$ is methyl.

Para. 6. The process of any one of Paras. 1-5, wherein $R^3$ and $R^4$ are each independently hydrogen or a substituted or unsubstituted $C_1$-$C_6$ alkyl.

Para. 7. The process of Para. 1 or 2, wherein the compound of Formula (II) is tert-butyl amine.

Para. 8. The process of any one of Paras. 1-7, wherein $R^5$ and $R^6$ are each independently hydrogen.

Para. 9. The process of any one of Paras. 1-8, wherein $R^7$ and $R^8$ in Formula (IIIa) together with the atoms to which they are attached form a $C_5$-$C_{10}$ aromatic ring.

Para. 10. The process of Para. 9, wherein the aromatic ring is a substituted or unsubstituted $C_6$ aromatic ring.

Para. 11. The process of Para. 1, wherein the compound of Formula (IIIa) or Formula (IVa) is represented by a compound of Formula (V):

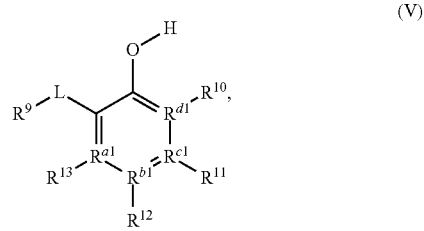

(V)

wherein:
L is a carbonyl, imine, acetal, or hemiacetal;
$R^9$ is hydrogen, halogen, hydroxyl, alkoxy, O-acyl;
$R^{10}$, $R^{11}$, $R^{12}$, and $R^{13}$ are each independently a hydrogen, a halogen, an alkoxy, a substituted or unsubstituted $C_1$-$C_{10}$ alkyl, a substituted or unsubstituted $C_3$-$C_{10}$ cycloalkyl, a substituted or unsubstituted aryl, a substituted or unsubstituted heterocyclyl, a substituted or unsubstituted heteroaryl, or two or more of $R^{10}$, $R^{11}$, $R^{12}$, and $R^{13}$ together with the atoms to which they are attached form a substituted or unsubstituted cycloalkyl, substituted or unsubstituted heterocyclyl, substituted or unsubstituted aromatic, or substituted or unsubstituted heteroaromatic ring;
$R^{a1}$, $R^{b1}$, $R^{c1}$, and $R^{d1}$ are each independently a C—R', N, or $N^+$—R',
wherein:
R' is any one of $R^{10}$, $R^{11}$, $R^{12}$, or $R^{13}$; and
when any one of $R^{a1}$, $R^{b1}$, $R^{c1}$, or $R^{d1}$ is N, the compound of Formula (V) does not include the corresponding $R^{10}$, $R^{11}$, $R^{12}$, or $R^{13}$ substituent.

Para. 12. The process of any one of Paras. 1 or 3-11, wherein L is a carbonyl and X is an amine.

Para. 13. The process of any one of Paras. 1 or 3-11, wherein L is converted to a carbonyl in situ from the imine, acetal, or hemiacetal, and X is converted to an amine in situ from a protected amine.

Para. 14. The process of any one of Paras. 1 or 3-11, wherein L is C=NR$^{e1}$, wherein R$^{e1}$ is hydrogen, a substituted or unsubstituted C$_1$-C$_{10}$ alkyl, a substituted or unsubstituted C$_3$-C$_{10}$ cycloalkyl, a substituted or unsubstituted aryl, a substituted or unsubstituted heterocyclyl, or a substituted or unsubstituted heteroaryl.

Para. 15. The process of any one of Paras. 11-14, wherein R$^{10}$, R$^{11}$, R$^{12}$, and R$^1$ are each independently hydrogen.

Para. 16. The process of any one of Paras. 11-14, wherein at least one of R$^{10}$, R$^{11}$, R$^{12}$, and R$^{13}$ is an alkoxy, halogen, or C$_1$-C$_6$ alkyl.

Para. 17. The process of any one of Paras. 11-14, wherein at least one of R$^{10}$, R$^{11}$, R$^{12}$, and R$^{13}$ are each independently hydrogen, and R$^{a1}$, R$^{b1}$, R$^{c1}$, and R$^{d1}$ are each independently C—R'.

Para. 18. The process of any one of Paras. 11-14, wherein R$^{10}$, R$^{11}$, R$^{12}$, and R$^{13}$ is an alkoxy, halogen, or C$_1$-C$_6$ alkyl; and R$^{a1}$, R$^{b1}$, R$^{c1}$, and R$^{d1}$ are each independently C—R'.

Para. 19. The process of any one of Paras. 11-18, wherein R$^9$ is hydrogen.

Para. 20. The process of any one of Paras. 15-19, wherein L is a carbonyl.

Para. 21. The process of any one of Paras. 1-11, wherein the compound of Formula (IIIa), Formula (IVa), or Formula (V) is

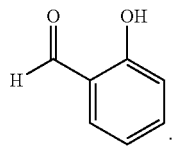

Para. 22. The process of any one of Paras. 1-21, wherein the condensation product is an imine.

Para. 23. The process of any one of Paras. 1-22, wherein the oxidant is selected from the group consisting of PhI(O(CO)R$^{f1}$)$_2$, PhI(OR$^{f1}$)$_2$, PhI(TFA)$_2$, PhIO, 2-iodoxybenzoic acid (IBX), Dess-Martin periodinane, M$_2$S$_2$O$_8$, R$^{f1}$COOI, R$^{g1}$OOR$^{h1}$, and O$_2$; wherein: R$^{f1}$ is hydrogen, a C$_1$-C$_6$ alkyl, or a substituted or unsubstituted aryl; R$^{g1}$ and R$^{h1}$ are each independently a hydrogen, a C$_1$-C$_6$ alkyl, or carboxyl group; and M is an alkali metal.

Para. 24. The process of Para. 23, wherein the oxidant is PhI(OAc)$_2$.

Para. 25. The process of any one of Paras. 1-24, wherein the hydroxylating or acyloxylating is conducted in the presence of one or more co-oxidants.

Para. 26. The process of any one of Paras. 1-25, wherein the hydroxylating or acyloxylating includes electrochemical oxidation.

Para. 27. The process of any one of Paras. 1-26, wherein the hydroxylating or acyloxylating is conducted in the presence of a heterogeneous or homogeneous catalyst.

Para. 28. The process of Para. 27, wherein catalyst comprises palladium or a palladium salt.

Para. 29. The process of Para. 28, wherein the catalyst is Pd(OAc)$_2$.

Para. 30. The process of any one of Paras. 1-29, wherein the hydroxylating or acyloxylating is conducted in the presence of one or more ligands.

Para. 31. The process of any one of Paras. 1-30, wherein the hydroxylating or acyloxylating is conducted in the presence of a base.

Para. 32. The process of Para. 31, wherein the base is present in an amount from about 0.01 to about 2 molar equivalents.

Para. 33. The process of any one of Paras. 1-32, wherein the hydroxylating or acyloxylating is conducted at a temperature from about 50° C. to about 180° C.

Para. 34. The process of any one of Paras. 1-33, wherein the alcohol deprotection occurs under neutral conditions, acidic conditions, basic conditions, or via transesterification.

Para. 35. The process of any one of Paras. 1-34, wherein the amino alcohol of Formula (I) is 2-amino-2-methylpropanol and the amine of Formula (II) is tert-butylamine.

Para. 36. The process of any one of Paras. 1-34, wherein X is a primary amine.

Para. 37. The process of any one of Paras. 1 or 12, wherein X is a primary amine.

As illustrated in the above Examples, the process of the present technology provides a process for efficiently preparing amino alcohols, and in particular 1,2 amino alcohols from primary amines.

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, or compositions, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

What is claimed is:

1. A process for the preparation of an amino alcohol, the process comprising:
   condensing a compound of Formula (II), a stereoisomer, a tautomer, or a salt thereof with a compound of Formula (IIIa) or Formula (IIIb), a stereoisomer, a tautomer, or a salt thereof to form a condensation product;
   hydroxylating or acyloxylating the condensation product in the presence of an oxidant to obtain a hydroxylation or acyloxylation product; and
   subjecting the hydroxylation or acyloxylation product to one or more subsequent reactions comprising a hydrolysis reaction, an aminolysis reaction, alcohol deprotection, or a combination of two or more thereof to obtain an amino alcohol of Formula (I);
   wherein:

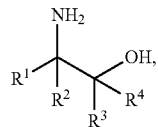
(I)

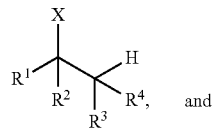
(II) and

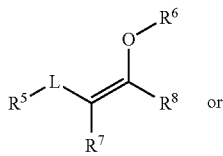
(IIIa) or

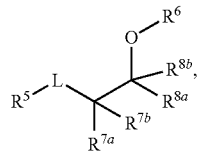
(IIIb)

L is a carbonyl, imine, acetal, or hemiacetal;
X is an amine or a protected amine;
$R^1$, $R^2$, $R^3$, and $R^4$ are each independently a hydrogen, a substituted or unsubstituted $C_1$-$C_{10}$ alkyl, a substituted or unsubstituted $C_3$-$C_{10}$ cycloalkyl, a substituted or unsubstituted aryl, a substituted or unsubstituted heterocyclyl, a substituted or unsubstituted heteroaryl, or two or more of $R^1$, $R^2$, $R^3$, and $R^4$ together with the atoms to which they are attached form a substituted or unsubstituted cycloalkyl, substituted or unsubstituted heterocyclyl, substituted or unsubstituted aromatic, or substituted or unsubstituted heteroaromatic ring;
$R^5$ is a hydrogen, a halogen, a hydroxyl, an alkoxy, an O-acyl, a substituted or unsubstituted $C_1$-$C_{10}$ alkyl, a substituted or unsubstituted $C_3$-$C_{10}$ cycloalkyl, a substituted or unsubstituted aryl, a substituted or unsubstituted heterocyclyl, or a substituted or unsubstituted heteroaryl;
$R^6$ is a hydrogen, a substituted or unsubstituted $C_1$-$C_{10}$ alkyl, a substituted or unsubstituted $C_3$-$C_{10}$ cycloalkyl, a substituted or unsubstituted aryl, a substituted or unsubstituted heterocyclyl, or a substituted or unsubstituted heteroaryl;
$R^7$ and $R^8$ in Formula (IIIa) are each independently a hydrogen, a substituted or unsubstituted $C_1$-$C_{10}$ alkyl, a substituted or unsubstituted $C_3$-$C_{10}$ cycloalkyl, a substituted or unsubstituted aryl, a substituted or unsubstituted heterocyclyl, a substituted or unsubstituted heteroaryl, or $R^7$ and $R^8$ together with the atoms to which they are attached form a substituted or unsubstituted aromatic or heteroaromatic ring; and
$R^{7a}$, $R^{7b}$, $R^{8a}$, and $R^{8b}$ in Formula (IIIb) are each independently a hydrogen, a substituted or unsubstituted $C_1$-$C_{10}$ alkyl, a substituted or unsubstituted $C_3$-$C_{10}$ cycloalkyl, a substituted or unsubstituted aryl, a substituted or unsubstituted heterocyclyl, a substituted or unsubstituted heteroaryl, or two or more of $R^{7a}$, $R^{7b}$, $R^{8a}$, and $R^{8b}$ together with the atoms to which they are attached form a substituted or unsubstituted cycloalkyl or heterocyclyl ring.

2. The process of claim 1, wherein $R^1$ is a substituted or unsubstituted $C_1$-$C_6$ alkyl.

3. The process of claim 2, wherein $R^1$ is selected from the group consisting of —CH$_3$, —CH$_2$CH$_2$Ph, and —CH$_2$C(CH$_3$)$_3$.

4. The process of claim 1, wherein $R^2$ is methyl.

5. The process of claim 1, wherein $R^3$ and $R^4$ are each dependently hydrogen or a substituted or unsubstituted $C_1$-$C_6$ alkyl.

6. The process of claim 1, wherein the compound of Formula (II) is tert-butyl amine.

7. The process of claim 1, wherein $R^5$ and $R^6$ are each independently hydrogen.

8. The process of claim 1, wherein $R^7$ and $R^8$ in Formula (IIIa) together with the atoms to which they are attached form a $C_5$-$C_{10}$ aromatic ring.

9. The process of claim 1, wherein the compound of Formula (IIIa) is represented by a compound of Formula (V):

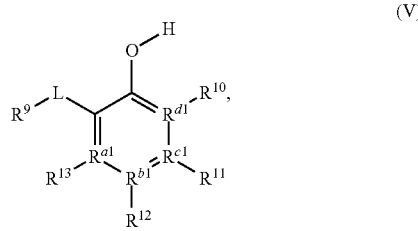

(V)

wherein:

L is a carbonyl, imine, acetal, or hemiacetal;

$R^9$ is hydrogen, halogen, hydroxyl, alkoxy, O-acyl;

$R^{10}$, $R^{11}$, $R^{12}$, and $R^{13}$ are each independently a hydrogen, a halogen, an alkoxy, a substituted or unsubstituted $C_1$-$C_{10}$ alkyl, a substituted or unsubstituted $C_3$-$C_{10}$ cycloalkyl, a substituted or unsubstituted aryl, a substituted or unsubstituted heterocyclyl, a substituted or unsubstituted heteroaryl, or two or more of $R^{10}$, $R^{11}$, $R^{12}$ and $R^{13}$ together with the atoms to which they are attached form a substituted or unsubstituted cycloalkyl, substituted or unsubstituted heterocyclyl, substituted or unsubstituted aromatic, or substituted or unsubstituted heteroaromatic ring;

$R^{a1}$, $R^{b1}$, $R^{c1}$, and $R^{d1}$ are each independently a C—R', N, or $N^+$—R', wherein:

R' is any one of $R^{10}$, $R^{11}$, $R^{12}$ and $R^{13}$; and when any one of $R^{a1}$, $R^{b1}$, $R^{c1}$, and $R^{d1}$ is N, the compound of Formula (V) does not include the corresponding $R^{10}$, $R^{11}$, $R^{12}$ and $R^{13}$ substituent.

10. The process of claim 1, wherein L is a carbonyl and X is an amine.

11. The process of claim 10, wherein X is —$NH_2$.

12. The process of claim 1, wherein L is C=$NR^{e1}$, wherein $R^{e1}$ is hydrogen, a substituted or unsubstituted $C_1$-$C_{10}$ alkyl, a substituted or unsubstituted $C_3$-$C_{10}$ cycloalkyl, a substituted or unsubstituted aryl, a substituted or unsubstituted heterocyclyl, or a substituted or unsubstituted heteroaryl.

13. The process of claim 9, wherein $R^{10}$, $R^{11}$, $R^{12}$ and $R^{13}$ are each independently hydrogen.

14. The process of claim 9, wherein at least one of $R^{10}$, $R^{11}$, $R^{12}$ and $R^{13}$ is an alkoxy, halogen, or $C_1$-$C_6$ alkyl.

15. The process of claim 9, wherein at least one of $R^{10}$, $R^{11}$, $R^{12}$ and $R^{13}$ are each independently hydrogen, and $R^{a1}$, $R^{b1}$, $R^{c1}$, and $R^{d1}$ are each independently C—R'.

16. The process of claim 9, wherein $R^9$ is hydrogen.

17. The process of claim 1, wherein the compound of Formula (IIIa) is

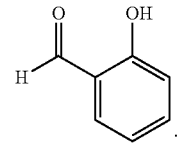

18. The process of claim 1, wherein the oxidant is selected from the group consisting of $PhI(O(CO)R^{f1})_2$, $PhI(OR^{f1})_2$, $PhI(TFA)_2$, PhIO, 2-iodoxybenzoic acid (IBX), Dess-Martin periodinane, $M_2S_2O_8$, $R^{f1}COOI$, $R^{g1}OOR^{h1}$, and $O_2$;

wherein:

$R^{f1}$ is hydrogen, a $C_1$-$C_6$ alkyl, or a substituted or unsubstituted aryl;

$R^{g1}$ and $R^{h1}$ are each independently a hydrogen, a $C_1$-$C_6$ alkyl, or carboxyl group; and M is an alkali metal.

19. The process of claim 1, which is performed in the presence of a catalyst, and wherein said catalyst comprises palladium or a palladium salt.

20. The process of claim 1, wherein the amino alcohol of Formula (I) is 2-amino-2-methylpropanol and the amine of Formula (II) is tert-butylamine.

* * * * *